(12) United States Patent
Wakarchuk et al.

(10) Patent No.: US 8,460,909 B2
(45) Date of Patent: Jun. 11, 2013

(54) ENGINEERED VERSIONS OF POLYSIALYLTRANSFERASES WITH ENHANCED ENZYMATIC PROPERTIES

(75) Inventors: Warren Wakarchuk, Ottawa (CA); Elizabeth Willis, Ottawa (CA); Michel Gilbert, Gatineau (CA)

(73) Assignee: National Research Council of Canada, Ottawa, Ontario (CA)

( * ) Notice: Subject to any disclaimer, the term of this patent is extended or adjusted under 35 U.S.C. 154(b) by 376 days.

(21) Appl. No.: 12/664,767

(22) PCT Filed: Jun. 13, 2008

(86) PCT No.: PCT/CA2008/001156
§ 371 (c)(1),
(2), (4) Date: Apr. 28, 2010

(87) PCT Pub. No.: WO2008/151448
PCT Pub. Date: Dec. 18, 2008

(65) Prior Publication Data
US 2010/0216185 A1 Aug. 26, 2010

Related U.S. Application Data

(60) Provisional application No. 60/944,391, filed on Jun. 15, 2007, provisional application No. 61/032,589, filed on Feb. 29, 2008.

(51) Int. Cl.
*C12N 9/10* (2006.01)
*C12P 21/06* (2006.01)
*C12P 19/00* (2006.01)
*C12Q 1/48* (2006.01)
*C07H 21/04* (2006.01)

(52) U.S. Cl.
USPC .............. 435/193; 435/68.1; 435/72; 435/15; 536/23.2

(58) Field of Classification Search
None
See application file for complete search history.

(56) References Cited

U.S. PATENT DOCUMENTS
2004/0029129 A1* 2/2004 Wang et al. ...................... 435/6

FOREIGN PATENT DOCUMENTS
WO 2007/087711 A1 8/2007

OTHER PUBLICATIONS

Frosch et al. Evidence for a common molecular origin of the capsule gene loci in gram-negative bacteria expressing group II capsular polysaccharides, Mol Microbiol 5(5): 1251-1263, 1991.*
Frosch et al. Mol. Microbiol. N (1991), 5: 1251-1263.*
Edwards et al. Mol. Microbiol. (1994), 14(1), 141-149.*
Database UniProt (online), Nov. 1, 1996, SiaD protein retrieved form EBI accession No. UNIPROT:Q51281.
Legaigneur, P. et al., Exploring the acceptor substrate recognition of the human beta-Galactoside alpha 2,6-sialyltransferase, Journal of Biological Chemistry, vol. 276, No. 24, Jun. 15, 2001, pp. 21608-21617.
Yu Hai et al., A multifunctional *Pasteurella multocida* sialyltransferase: A powerful tool for the synthesis of sialoside libraries, Journal of the American Chemical Society, vol. 127, No. 50, Dec. 2005, pp. 17618-17619.

* cited by examiner

*Primary Examiner* — Anand Desai
*Assistant Examiner* — Iqbal H Chowdhury
(74) *Attorney, Agent, or Firm* — Senia Patenaude

(57) ABSTRACT

The invention relates to poly-sialyltransferse polypeptides with enhanced solubility and activity and methods of using the poly-sialyltransferases for production of poly-sialylated end products, e.g., oligosaccharides, glycoproteins and glycolipids.

10 Claims, 15 Drawing Sheets

SEQUENCE LISTING

<160> NUMBER OF SEQ ID NOS: 11

<210> SEQ ID NO 1
<211> LENGTH: 495
<212> TYPE: PRT
<213> ORGANISM: Neisseria meningitidis

<400> SEQUENCE: 1

Met Leu Lys Lys Ile Lys Lys Ala Leu Phe Gln Pro Lys Lys Phe Phe
1               5                   10                  15

Gln Asp Ser Met Trp Leu Thr Thr Ser Pro Phe Tyr Leu Thr Pro Pro
            20                  25                  30

Arg Asn Asn Leu Phe Val Ile Ser Asn Leu Gly Gln Leu Asn Gln Val
        35                  40                  45

Gln Ser Leu Ile Lys Ile Gln Lys Leu Thr Asn Asn Leu Leu Val Ile
    50                  55                  60

Leu Tyr Thr Ser Lys Asn Leu Lys Met Pro Lys Leu Val His Gln Ser
65                  70                  75                  80

Ala Asn Lys Asn Leu Phe Glu Ser Ile Tyr Leu Phe Glu Leu Pro Arg
                85                  90                  95

Ser Pro Asn Asn Ile Thr Pro Lys Lys Leu Leu Tyr Ile Tyr Arg Ser
            100                 105                 110

Tyr Lys Lys Ile Leu Asn Ile Ile Gln Pro Ala His Leu Tyr Met Leu
        115                 120                 125

Ser Phe Thr Gly His Tyr Ser Tyr Leu Ile Ser Ile Ala Lys Lys Lys
    130                 135                 140

Asn Ile Thr Thr His Leu Ile Asp Glu Gly Thr Gly Thr Tyr Ala Pro
145                 150                 155                 160

Leu Leu Glu Ser Phe Ser Tyr His Pro Thr Lys Leu Glu Arg Tyr Leu
                165                 170                 175

Ile Gly Asn Asn Leu Asn Ile Lys Gly Tyr Ile Asp His Phe Asp Ile
            180                 185                 190

Leu His Val Pro Phe Pro Glu Tyr Ala Lys Lys Ile Phe Asn Ala Lys
        195                 200                 205

```
Lys Tyr Asn Arg Phe Phe Ala His Ala Gly Gly Ile Ser Ile Asn Asn
            210                 215                 220

Asn Ile Ala Asn Leu Gln Lys Lys Tyr Gln Ile Ser Lys Asn Asp Tyr
225                 230                 235                 240

Ile Phe Val Ser Gln Arg Tyr Pro Ile Ser Asp Asp Leu Tyr Tyr Lys
            245                 250                 255

Ser Ile Val Glu Ile Leu Asn Ser Ile Ser Leu Gln Ile Lys Gly Lys
            260                 265                 270

Ile Phe Ile Lys Leu His Pro Lys Glu Met Gly Asn Asn Tyr Val Met
            275                 280                 285

Ser Leu Phe Leu Asn Met Val Glu Ile Asn Pro Arg Leu Val Val Ile
            290                 295                 300

Asn Glu Pro Pro Phe Leu Ile Glu Pro Leu Ile Tyr Leu Thr Asn Pro
305                 310                 315                 320

Lys Gly Ile Ile Gly Leu Ala Ser Ser Ser Leu Ile Tyr Thr Pro Leu
            325                 330                 335

Leu Ser Pro Ser Thr Gln Cys Leu Ser Ile Gly Glu Leu Ile Ile Asn
            340                 345                 350

Leu Ile Gln Lys Tyr Ser Met Val Glu Asn Thr Glu Met Ile Gln Glu
            355                 360                 365

His Leu Glu Ile Ile Lys Lys Phe Asn Phe Ile Asn Ile Leu Asn Asp
            370                 375                 380

Leu Asn Gly Val Ile Ser Asn Pro Leu Phe Lys Thr Glu Glu Thr Phe
385                 390                 395                 400

Glu Thr Leu Leu Lys Ser Ala Glu Phe Ala Tyr Lys Ser Lys Asn Tyr
            405                 410                 415

Phe Gln Ala Ile Phe Tyr Trp Gln Leu Ala Ser Lys Asn Asn Ile Thr
            420                 425                 430

Leu Leu Gly His Lys Ala Leu Trp Tyr Tyr Asn Ala Leu Tyr Asn Val
            435                 440                 445

Lys Gln Ile Tyr Lys Met Glu Tyr Ser Asp Ile Phe Tyr Ile Asp Asn
            450                 455                 460

Ile Ser Val Asp Phe His Ser Lys Asp Lys Leu Thr Trp Glu Lys Ile
465                 470                 475                 480

Lys His Tyr Tyr Tyr Ser Ala Asp Asn Arg Ile Gly Arg Asp Arg
            485                 490                 495

<210> SEQ ID NO 2
<211> LENGTH: 859
<212> TYPE: PRT
<213> ORGANISM: Artificial
<220> FEATURE:
<223> OTHER INFORMATION: MalE-PstNm(-19aa, PST-29)

<400> SEQUENCE: 2

Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
            35                  40                  45

Pro Gln Val Ala Ala Thr Gly Asp Gly Pro Asp Ile Ile Phe Trp Ala
        50                  55                  60

His Asp Arg Phe Gly Gly Tyr Ala Gln Ser Gly Leu Leu Ala Glu Ile
65                  70                  75                  80
```

```
                         -continued

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
    290                 295                 300

Leu Lys Ser Tyr Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Arg
        355                 360                 365

Ile Thr Lys Gly Gly Gly His Ile Phe Asn Pro Arg Gly Ser His Met
    370                 375                 380

Trp Leu Thr Thr Ser Pro Phe Tyr Leu Thr Pro Arg Asn Asn Leu
385                 390                 395                 400

Phe Val Ile Ser Asn Leu Gly Gln Leu Asn Gln Val Gln Ser Leu Ile
                405                 410                 415

Lys Ile Gln Lys Leu Thr Asn Asn Leu Leu Val Ile Leu Tyr Thr Ser
            420                 425                 430

Lys Asn Leu Lys Met Pro Lys Leu Val His Gln Ser Ala Asn Lys Asn
        435                 440                 445

Leu Phe Glu Ser Ile Tyr Leu Phe Glu Leu Pro Arg Ser Pro Asn Asn
    450                 455                 460

Ile Thr Pro Lys Lys Leu Leu Tyr Ile Tyr Arg Ser Tyr Lys Lys Ile
465                 470                 475                 480

Leu Asn Ile Ile Gln Pro Ala His Leu Tyr Met Leu Ser Phe Thr Gly
                485                 490                 495

His Tyr Ser Tyr Leu Ile Ser Ile Ala Lys Lys Asn Ile Thr Thr
            500                 505                 510
```

His Leu Ile Asp Glu Gly Thr Gly Thr Tyr Ala Pro Leu Leu Glu Ser
        515                 520                 525

Phe Ser Tyr His Pro Thr Lys Leu Glu Arg Asn Leu Ile Gly Asn Asn
        530                 535                 540

Leu Asn Ile Lys Gly Tyr Ile Asp His Phe Asp Ile Leu His Val Pro
545                 550                 555                 560

Phe Pro Glu Tyr Ala Lys Lys Ile Phe Asn Ala Lys Lys Tyr Asn Arg
                565                 570                 575

Phe Phe Ala His Ala Gly Gly Ile Ser Ile Asn Asn Asn Ile Ala Asn
            580                 585                 590

Leu Gln Lys Lys Tyr Gln Ile Ser Lys Asn Asp Tyr Ile Phe Val Ser
        595                 600                 605

Gln Arg Tyr Pro Ile Ser Asp Asp Leu Tyr Tyr Lys Ser Ile Val Glu
        610                 615                 620

Ile Leu Asn Ser Ile Ser Leu Gln Ile Lys Gly Lys Ile Phe Ile Lys
625                 630                 635                 640

Leu His Pro Lys Glu Met Gly Asn Asn Tyr Val Met Ser Leu Phe Leu
                645                 650                 655

Asn Met Val Glu Ile Asn Pro Arg Leu Val Val Ile Asn Glu Pro Pro
            660                 665                 670

Phe Leu Ile Glu Pro Leu Ile Tyr Leu Thr Asn Pro Lys Gly Ile Ile
        675                 680                 685

Gly Leu Ala Ser Ser Ser Leu Ile Tyr Thr Pro Leu Leu Ser Pro Ser
        690                 695                 700

Thr Gln Cys Leu Ser Ile Gly Glu Leu Ile Ile Asn Leu Ile Gln Lys
705                 710                 715                 720

Tyr Ser Met Val Glu Asn Thr Glu Met Ile Gln Glu His Leu Glu Ile
                725                 730                 735

Ile Lys Lys Phe Asn Phe Ile Asn Ile Leu Asn Asp Leu Asn Gly Val
            740                 745                 750

Ile Ser Asn Pro Leu Phe Lys Thr Glu Glu Thr Phe Glu Thr Leu Leu
        755                 760                 765

Lys Ser Ala Glu Phe Ala Tyr Lys Ser Lys Asn Tyr Phe Gln Ala Ile
        770                 775                 780

Phe Tyr Trp Gln Leu Ala Ser Lys Asn Asn Ile Thr Leu Leu Gly His
785                 790                 795                 800

Lys Ala Leu Trp Tyr Tyr Asn Ala Leu Tyr Asn Val Lys Gln Ile Tyr
                805                 810                 815

Lys Met Glu Tyr Ser Asp Ile Phe Tyr Ile Asp Asn Ile Ser Val Asp
            820                 825                 830

Phe His Ser Lys Asp Lys Leu Thr Trp Glu Lys Ile Lys His Tyr Tyr
        835                 840                 845

Tyr Phe Ala Asp Asn Arg Ile Gly Arg Asp Arg
    850                 855

<210> SEQ ID NO 3
<211> LENGTH: 476
<212> TYPE: PRT
<213> ORGANISM: Artificial
<220> FEATURE:
<223> OTHER INFORMATION: PstNm(-19aa, PST-29)

<400> SEQUENCE: 3

Met Trp Leu Thr Thr Ser Pro Phe Tyr Leu Thr Pro Pro Arg Asn Asn
1               5                   10                  15

```
Leu Phe Val Ile Ser Asn Leu Gly Gln Leu Asn Gln Val Gln Ser Leu
                 20                  25                  30

Ile Lys Ile Gln Lys Leu Thr Asn Asn Leu Val Ile Leu Tyr Thr
         35                  40                  45

Ser Lys Asn Leu Lys Met Pro Lys Leu Val His Gln Ser Ala Asn Lys
 50                  55                  60

Asn Leu Phe Glu Ser Ile Tyr Leu Phe Glu Leu Pro Arg Ser Pro Asn
 65                  70                  75                  80

Asn Ile Thr Pro Lys Lys Leu Leu Tyr Ile Tyr Arg Ser Tyr Lys Lys
                 85                  90                  95

Ile Leu Asn Ile Ile Gln Pro Ala His Leu Tyr Met Leu Ser Phe Thr
                100                 105                 110

Gly His Tyr Ser Tyr Leu Ile Ser Ile Ala Lys Lys Lys Asn Ile Thr
                115                 120                 125

Thr His Leu Ile Asp Glu Gly Thr Gly Thr Tyr Ala Pro Leu Leu Glu
130                 135                 140

Ser Phe Ser Tyr His Pro Thr Lys Leu Glu Arg Asn Leu Ile Gly Asn
145                 150                 155                 160

Asn Leu Asn Ile Lys Gly Tyr Ile Asp His Phe Asp Ile Leu His Val
                165                 170                 175

Pro Phe Pro Glu Tyr Ala Lys Lys Ile Phe Asn Ala Lys Lys Tyr Asn
                180                 185                 190

Arg Phe Phe Ala His Ala Gly Gly Ile Ser Ile Asn Asn Asn Ile Ala
                195                 200                 205

Asn Leu Gln Lys Lys Tyr Gln Ile Ser Lys Asn Asp Tyr Ile Phe Val
210                 215                 220

Ser Gln Arg Tyr Pro Ile Ser Asp Asp Leu Tyr Tyr Lys Ser Ile Val
225                 230                 235                 240

Glu Ile Leu Asn Ser Ile Ser Leu Gln Ile Lys Gly Lys Ile Phe Ile
                245                 250                 255

Lys Leu His Pro Lys Glu Met Gly Asn Asn Tyr Val Met Ser Leu Phe
                260                 265                 270

Leu Asn Met Val Glu Ile Asn Pro Arg Leu Val Val Ile Asn Glu Pro
                275                 280                 285

Pro Phe Leu Ile Glu Pro Leu Ile Tyr Leu Thr Asn Pro Lys Gly Ile
                290                 295                 300

Ile Gly Leu Ala Ser Ser Ser Leu Ile Tyr Thr Pro Leu Leu Ser Pro
305                 310                 315                 320

Ser Thr Gln Cys Leu Ser Ile Gly Glu Leu Ile Ile Asn Leu Ile Gln
                325                 330                 335

Lys Tyr Ser Met Val Glu Asn Thr Glu Met Ile Gln Glu His Leu Glu
                340                 345                 350

Ile Ile Lys Lys Phe Asn Phe Ile Asn Ile Leu Asn Asp Leu Asn Gly
                355                 360                 365

Val Ile Ser Asn Pro Leu Phe Lys Thr Glu Glu Thr Phe Glu Thr Leu
370                 375                 380

Leu Lys Ser Ala Glu Phe Ala Tyr Lys Ser Lys Asn Tyr Phe Gln Ala
385                 390                 395                 400

Ile Phe Tyr Trp Gln Leu Ala Ser Lys Asn Asn Ile Thr Leu Leu Gly
                405                 410                 415

His Lys Ala Leu Trp Tyr Tyr Asn Ala Leu Tyr Asn Val Lys Gln Ile
                420                 425                 430

Tyr Lys Met Glu Tyr Ser Asp Ile Phe Tyr Ile Asp Asn Ile Ser Val
                435                 440                 445
```

```
Asp Phe His Ser Lys Asp Lys Leu Thr Trp Glu Lys Ile Lys His Tyr
    450                 455                 460

Tyr Tyr Phe Ala Asp Asn Arg Ile Gly Arg Asp Arg
465                 470                 475

<210> SEQ ID NO 4
<211> LENGTH: 847
<212> TYPE: PRT
<213> ORGANISM: Artificial
<220> FEATURE:
<223> OTHER INFORMATION: MalE-PSTNm(-32aa, PST-30)

<400> SEQUENCE: 4

Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
                20                  25                  30

Gly Ile Lys Val Thr Val Glu His Pro Asp Lys Leu Glu Glu Lys Phe
            35                  40                  45

Pro Gln Val Ala Ala Thr Gly Asp Gly Pro Asp Ile Ile Phe Trp Ala
        50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
    290                 295                 300

Leu Lys Ser Tyr Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335
```

-continued

```
Met Ser Ala Phe Trp Tyr Ala Val Arg Thr Ala Val Ile Asn Ala Ala
                340                 345                 350
Ser Gly Arg Gln Thr Val Asp Glu Ala Leu Lys Asp Ala Gln Thr Arg
            355                 360                 365
Ile Thr Lys Gly Gly His Ile Phe Asn Pro Arg Gly Ser His Met
370                 375                 380
Arg Asn Asn Leu Phe Val Ile Ser Asn Leu Gly Gln Leu Asn Gln Val
385                 390                 395                 400
Gln Ser Leu Ile Lys Ile Gln Lys Leu Thr Asn Asn Leu Leu Val Ile
                405                 410                 415
Leu Tyr Thr Ser Lys Asn Leu Lys Met Pro Lys Leu Val His Gln Ser
            420                 425                 430
Ala Asn Lys Asn Leu Phe Glu Ser Ile Tyr Leu Phe Glu Leu Pro Arg
        435                 440                 445
Ser Pro Asn Asn Ile Thr Pro Lys Lys Leu Leu Tyr Ile Tyr Arg Ser
    450                 455                 460
Tyr Lys Lys Ile Leu Asn Ile Ile Gln Pro Ala His Leu Tyr Met Leu
465                 470                 475                 480
Ser Phe Thr Gly His Tyr Ser Tyr Leu Ile Ser Ile Ala Lys Lys Lys
                485                 490                 495
Asn Ile Thr Thr His Leu Ile Asp Glu Gly Thr Gly Thr Tyr Ala Pro
            500                 505                 510
Leu Leu Glu Ser Phe Ser Tyr His Pro Thr Lys Leu Glu Arg Asn Leu
        515                 520                 525
Ile Gly Asn Asn Leu Asn Ile Lys Gly Tyr Ile Asp His Phe Asp Ile
    530                 535                 540
Leu His Val Pro Phe Pro Glu Tyr Ala Lys Lys Ile Phe Asn Ala Lys
545                 550                 555                 560
Lys Tyr Asn Arg Phe Phe Ala His Ala Gly Gly Ile Ser Ile Asn Asn
                565                 570                 575
Asn Ile Ala Asn Leu Gln Lys Lys Tyr Gln Ile Ser Lys Asn Asp Tyr
            580                 585                 590
Ile Phe Val Ser Gln Arg Tyr Pro Ile Ser Asp Asp Leu Tyr Tyr Lys
        595                 600                 605
Ser Ile Val Glu Ile Leu Asn Ser Ile Ser Leu Gln Ile Lys Gly Lys
    610                 615                 620
Ile Phe Ile Lys Leu His Pro Lys Glu Met Gly Asn Asn Tyr Val Met
625                 630                 635                 640
Ser Leu Phe Leu Asn Met Val Glu Ile Asn Pro Arg Leu Val Val Ile
                645                 650                 655
Asn Glu Pro Pro Phe Leu Ile Glu Pro Leu Ile Tyr Leu Thr Asn Pro
            660                 665                 670
Lys Gly Ile Ile Gly Leu Ala Ser Ser Ser Leu Ile Tyr Thr Pro Leu
        675                 680                 685
Leu Ser Pro Ser Thr Gln Cys Leu Ser Ile Gly Glu Leu Ile Ile Asn
    690                 695                 700
Leu Ile Gln Lys Tyr Ser Met Val Glu Asn Thr Glu Met Ile Gln Glu
705                 710                 715                 720
His Leu Glu Ile Ile Lys Lys Phe Asn Phe Ile Asn Ile Leu Asn Asp
                725                 730                 735
Leu Asn Gly Val Ile Ser Asn Pro Leu Phe Lys Thr Glu Glu Thr Phe
            740                 745                 750
Glu Thr Leu Leu Lys Ser Ala Glu Phe Ala Tyr Lys Ser Lys Asn Tyr
        755                 760                 765
```

```
Phe Gln Ala Ile Phe Tyr Trp Gln Leu Ala Ser Lys Asn Asn Ile Thr
            770                 775                 780

Leu Leu Gly His Lys Ala Leu Trp Tyr Tyr Asn Ala Leu Tyr Asn Val
785                 790                 795                 800

Lys Gln Ile Tyr Lys Met Glu Tyr Ser Asp Ile Phe Tyr Ile Asp Asn
                805                 810                 815

Ile Ser Val Asp Phe His Ser Lys Asp Lys Leu Thr Trp Glu Lys Ile
                820                 825                 830

Lys His Tyr Tyr Tyr Phe Ala Asp Asn Arg Ile Gly Arg Asp Arg
                835                 840                 845

<210> SEQ ID NO 5
<211> LENGTH: 463
<212> TYPE: PRT
<213> ORGANISM: Artificial
<220> FEATURE:
<223> OTHER INFORMATION: PSTNm(-32aa, PST-30)

<400> SEQUENCE: 5

Arg Asn Asn Leu Phe Val Ile Ser Asn Leu Gly Gln Leu Asn Gln Val
1               5                   10                  15

Gln Ser Leu Ile Lys Ile Gln Lys Leu Thr Asn Asn Leu Leu Val Ile
                20                  25                  30

Leu Tyr Thr Ser Lys Asn Leu Lys Met Pro Lys Leu Val His Gln Ser
                35                  40                  45

Ala Asn Lys Asn Leu Phe Glu Ser Ile Tyr Leu Phe Glu Leu Pro Arg
            50                  55                  60

Ser Pro Asn Asn Ile Thr Pro Lys Lys Leu Leu Tyr Ile Tyr Arg Ser
65                  70                  75                  80

Tyr Lys Lys Ile Leu Asn Ile Gln Pro Ala His Leu Tyr Met Leu
                85                  90                  95

Ser Phe Thr Gly His Tyr Ser Tyr Leu Ile Ser Ile Ala Lys Lys Lys
                100                 105                 110

Asn Ile Thr Thr His Leu Ile Asp Glu Gly Thr Gly Thr Tyr Ala Pro
            115                 120                 125

Leu Leu Glu Ser Phe Ser Tyr His Pro Thr Lys Leu Glu Arg Asn Leu
            130                 135                 140

Ile Gly Asn Asn Leu Asn Ile Lys Gly Tyr Ile Asp His Phe Asp Ile
145                 150                 155                 160

Leu His Val Pro Phe Pro Glu Tyr Ala Lys Lys Ile Phe Asn Ala Lys
                165                 170                 175

Lys Tyr Asn Arg Phe Phe Ala His Ala Gly Gly Ile Ser Ile Asn Asn
            180                 185                 190

Asn Ile Ala Asn Leu Gln Lys Lys Tyr Gln Ile Ser Lys Asn Asp Tyr
        195                 200                 205

Ile Phe Val Ser Gln Arg Tyr Pro Ile Ser Asp Leu Tyr Tyr Lys
            210                 215                 220

Ser Ile Val Glu Ile Leu Asn Ser Ile Ser Leu Gln Ile Lys Gly Lys
225                 230                 235                 240

Ile Phe Ile Lys Leu His Pro Lys Glu Met Gly Asn Asn Tyr Val Met
                245                 250                 255

Ser Leu Phe Leu Asn Met Val Glu Ile Asn Pro Arg Leu Val Val Ile
            260                 265                 270

Asn Glu Pro Pro Phe Leu Ile Glu Pro Leu Ile Tyr Leu Thr Asn Pro
                275                 280                 285
```

```
Lys Gly Ile Ile Gly Leu Ala Ser Ser Ser Leu Ile Tyr Thr Pro Leu
            290                 295                 300

Leu Ser Pro Ser Thr Gln Cys Leu Ser Ile Gly Glu Leu Ile Ile Asn
305                 310                 315                 320

Leu Ile Gln Lys Tyr Ser Met Val Glu Asn Thr Glu Met Ile Gln Glu
                325                 330                 335

His Leu Glu Ile Ile Lys Lys Phe Asn Phe Ile Asn Ile Leu Asn Asp
            340                 345                 350

Leu Asn Gly Val Ile Ser Asn Pro Leu Phe Lys Thr Glu Glu Thr Phe
        355                 360                 365

Glu Thr Leu Leu Lys Ser Ala Glu Phe Ala Tyr Lys Ser Lys Asn Tyr
    370                 375                 380

Phe Gln Ala Ile Phe Tyr Trp Gln Leu Ala Ser Lys Asn Asn Ile Thr
385                 390                 395                 400

Leu Leu Gly His Lys Ala Leu Trp Tyr Tyr Asn Ala Leu Tyr Asn Val
                405                 410                 415

Lys Gln Ile Tyr Lys Met Glu Tyr Ser Asp Ile Phe Tyr Ile Asp Asn
            420                 425                 430

Ile Ser Val Asp Phe His Ser Lys Asp Lys Leu Thr Trp Glu Lys Ile
        435                 440                 445

Lys His Tyr Tyr Tyr Phe Ala Asp Asn Arg Ile Gly Arg Asp Arg
    450                 455                 460

<210> SEQ ID NO 6
<211> LENGTH: 53
<212> TYPE: PRT
<213> ORGANISM: Artificial
<220> FEATURE:
<223> OTHER INFORMATION: MalE-PSTNm(-29aa, PST-19,PST-32)

<400> SEQUENCE: 6

Met Leu Lys Lys Ile Lys Lys Ala Leu Phe Gln Pro Lys Lys Phe Phe
1               5                   10                  15

Gln Asp Ser Met Trp Leu Thr Thr Ser Pro Phe Tyr Leu Thr Pro Pro
            20                  25                  30

Arg Asn Asn Leu Ph

```
<400> SEQUENCE: 8

Asp Val Phe Arg Cys Asn Gln Phe Tyr Phe Glu Xaa
1               5                   10

<210> SEQ ID NO 9
<211> LENGTH: 9
<212> TYPE: PRT
<213> ORGANISM: Artificial Sequence
<220> FEATURE:
<223> OTHER INFORMATION: Bacterial sialyltransferase motif B

<400> SEQUENCE: 9

Arg Ile Thr Ser Gly Val Tyr Met Cys
1               5

<210> SEQ ID NO 10
<211> LENGTH: 41
<212> TYPE: DNA
<213> ORGANISM: Artificial Sequence
<220> FEATURE:
<223> OTHER INFORMATION: 5' primer for amplifying E. coli PST

<400> SEQUENCE: 10
aaggtataag acatatgata tttgatgcta gtttaaagaa g                     41

<210> SEQ ID NO 11
<211> LENGTH: 42
<212> TYPE: DNA
<213> ORGANISM: Artificial Sequence
<220> FEATURE:
<223> OTHER INFORMATION: 3' primer for amplifying E. coli PST

<400> SEQUENCE: 11
cctaggtcga cttactcccc caagaaaatc cttttatcgt gc                    42
```

US 8,460,909 B2

ENGINEERED VERSIONS OF POLYSIALYLTRANSFERASES WITH ENHANCED ENZYMATIC PROPERTIES

CROSS REFERENCES TO RELATED APPLICATIONS

This application is a National Phase application of the International Appl. No. PCT/CA2008/001156 filed Jun. 13, 2008, which claims the benefit of U.S. Provisional Application No. 60/944,391, filed Jun. 15, 2007, and U.S. Provisional Application No. 61/032,589, filed Feb. 29, 2008, both of which are incorporated herein by reference for all purposes.

FIELD OF THE INVENTION

The invention relates to poly-sialyltransferase (PST) polypeptides with enhanced solubility and activity and methods of using the poly-sialyltransferases for production of poly-sialylated end products, e.g., oligosaccharides, glycoproteins and glycolipids.

BACKGROUND OF THE INVENTION

Glycoproteins, glycolipids and polysaccharides are present on the cell surface of mammalian cells and are central molecules in many biological processes. They participate in cell-cell recognition, cell differentiation and various receptor-ligand interactions throughout biology. Many of these biologically active glycans contain an essential 9-carbon sugar that is known as sialic acid, or N-acetyl-neuraminic acid (NeuAc).

Some bacterial pathogens that invade the mammalian host have taken advantage of the presence of sialic acid containing glycoconjugates on the host. These bacteria display some of these same carbohydrate chains on bacterial cell surfaces, and indeed a role for these carbohydrates in pathogenesis has been demonstrated. See, e.g., Kahler, C. M. and Stephens, D. S., *Crit. Rev Microbiol,* 24:281-334 (1998), and Moran, A. P. et al., *FEMS Immunol Med Microbiol,* 16:105-115 (1996). It is thought that the presence of the carbohydrate mimics allows the pathogens to escape detection by the immune system since these molecules are not considered foreign. Further, the presence of these carbohydrates presents a physical barrier for the killing action of serum complement. See, e.g., Vogel, U. et al., *Med Microbiol Immunol (Berl),* 185:81-87 (1996). Finally it may be that certain pathogens use normal human receptors that recognize their surface carbohydrate structures as a means of aiding transmission (or colonization of the host, although this mechanism remains unproven for many of these pathogens). See, e.g., Preston, A. et al., *Crit Rev Microbiol,* 22:139-180 (1996) and Harvey, H. A. et al., *Mol Microbiol,* 36:1059-1070 (2000).

Capsular polysaccharides from group B *Neisseria meningitidis* and *Escherichia coli* K1 have sialic acid in linkages that are molecular mimics of the polysialic acid (PSA) structure seen mainly in the mammalian neural cell adhesion molecule, a brain specific protein integral to neuronal function. Thus they are found as a homo-polymer of α-2,8-linked Neu5Ac, and also as homo-polymers of α-2,9-linked residues, as a co-polymer in which the linkage is mixed α-2,8/α-2,9, and finally as polymers in which other sugars are included, as in the Group Y and W *Neisseria meningitidis*. These polysialic acid capsules are required for neuro-invasive disease in the case of *E. coli, N. meningitidis* and *P. haemolytica*. See, e.g., Silver, R. P., and E. R. Vimr. 1990. Polysialic acid capsule of *Escherichia coli* K1, p. 39-60. In B. H. Iglewski, and V. L. Clark (ed.), *Molecular basis of microbial pathogenesis.* Academic Press, Inc., San Diego, Calif. It is important to note that because many of these pathogens are specific for a human host, data from animal model infections may not have shown all of the true functions of these glycoconjugates.

To date there has been little detailed work on the fundamental aspects of the sialyltransferase enzymology from bacterial pathogens. It is possible to express, purify and crystallize some of those enzymes responsible for LOS sialylation. See, e.g., Gilbert, M. et al., *J Biol Chem,* 271:28271-28276 (1996); Gilbert, M. et al., *J Biol Chem,* 275:3896-3906 (2000); Chiu, C. P. et al., *Nat. Struct. Mol. Biol.,* 11:163-170 (2004); and Yu, H. et al., *J. Am. Chem. Soc.,* 127:17618-17619 (2005). However no such work has been done with those enzymes involved in the generation of the sialic acid homopolymeric capsules.

The genetic loci for the PSA capsule production have been identified in both *E. coli* and *N. meningitidis*, and some work has been done on the recombinant enzymes (NeuS) from *E. coli* K1, and K92. See, e.g., Cho, J. and Troy F A, I. I., *PNAS,* 91:11427-11431 (1994) and Shen, G. J. et al., *J. Biol. Chem.,* 274:35139-35146 (1999). But again no detailed enzymology on the isolated sialyltransferase has been reported. The study of the enzymology has been hampered by the poor solubility of the enzyme thus hampering the production of polysialic acid conjugates in vitro. The present invention solves this and other needs.

BRIEF SUMMARY OF THE INVENTION

The invention provides truncated polysialic acid transferase (PST) polypeptides that transfer a sialic acid moiety from a donor substrate to an appropriate acceptor substrate. In one embodiment, the truncated PST polypeptides comprise an amino acid sequence with 95% identity to amino acids 33-495 of SEQ ID NO:1. In another embodiment the truncated PST polypeptides comprise an amino acid sequence with 95% identity to amino acids 20-495 of SEQ ID NO:1. Preferably, the truncated PST polypeptides are more soluble than a full length PST polypeptide consisting of amino acids 1-495 of SEQ ID NO:1. The truncated PST polypeptides of the invention do not comprise an amino acid sequence consisting of amino acids 1-495 of SEQ ID NO:1.

In one aspect, the truncated PST polypeptides comprise an MBP tag. In another aspect, the acceptor substrate sialylated by the truncated PST polypeptides is, e.g., a glycopeptide, a glycoprotein, a glycolipid, or a ganglioside. In a further aspect, the acceptor substrate is a glycoprotein, e.g., Factor IX, erythropoietin (EPO), Transferrin, and Fetuin. In preferred embodiments, the glycoprotein substrate is a human protein.

The present invention provides a method of producing a poly-sialylated product saccharide by contacting an acceptor substrate, e.g., an oligosaccharide or saccharide, with a truncated PST polypeptide and a donor substrate comprising a sialic acid moiety and allowing transfer of the sialic acid moiety to the acceptor saccharide to occur, thereby producing the poly-sialylated product saccharide.

The present invention provides a method of producing a poly-sialylated protein or peptide by contacting an acceptor substrate, e.g., an appropriate protein or peptide, with a truncated PST polypeptide and a donor substrate comprising a sialic acid moiety and allowing transfer of the sialic acid moiety to the acceptor saccharide to occur, thereby producing the poly-sialylated protein or peptide.

The present invention provides a method of producing a poly-sialylated glycolipid or gangliosides by contacting an acceptor substrate, e.g., an appropriate glycolipid or ganglioside, with a truncated PST polypeptide and a donor substrate comprising a sialic acid moiety and allowing transfer of the sialic acid moiety to the acceptor saccharide to occur, thereby producing the poly-sialylated glycolipid or ganglioside.

DETAILED DESCRIPTION OF THE INVENTION

I. Introduction

Figure 1:
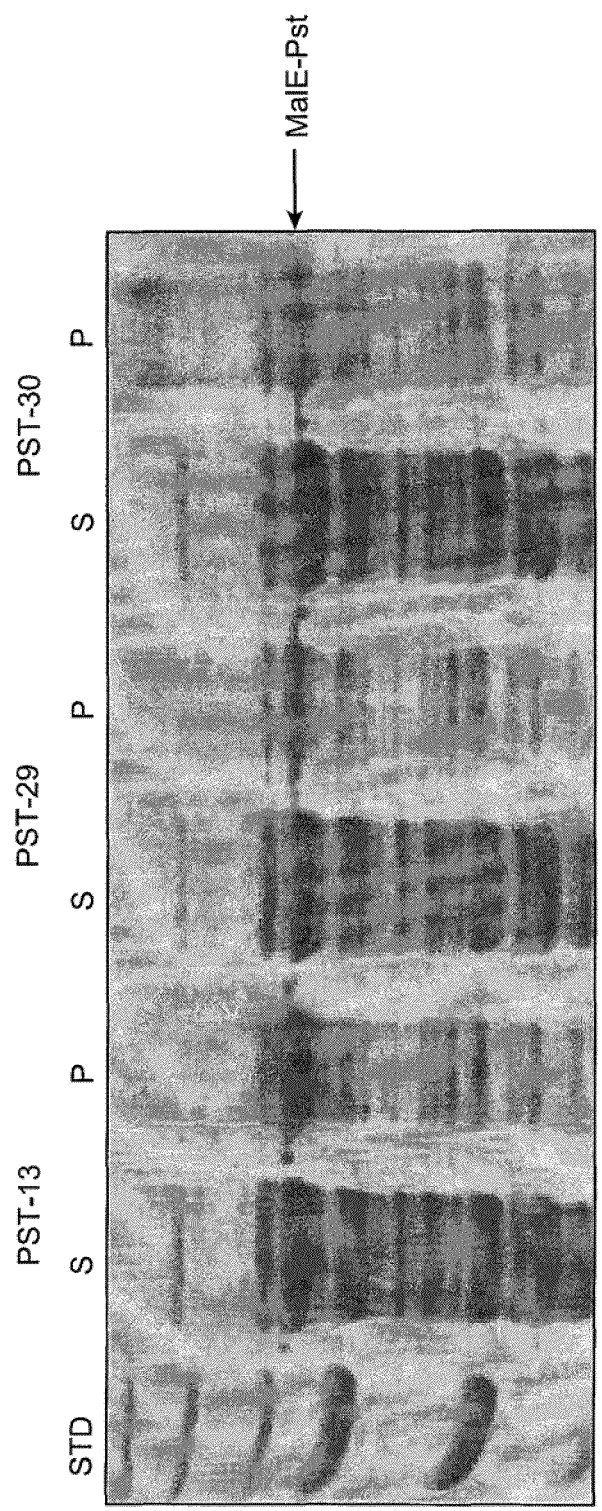
FIG. 1 SDS-PAGE analysis of the PST N-terminal truncations. PST-13 (MalE-full length PST), PST-29 (MalE-PST-Δ19) and PST-30 (MalE-PST-Δ32) were analyzed for solubility. "P" indicates the pellet fraction and "S" indicates the supernatant (soluble) fraction.

Poly-sialyltransferase (PST) polypeptides have been constructed to efficiently produce poly-sialylated products, e.g., oligosaccharides, glycoproteins, and glycolipids that contain poly-sialic acid groups. Truncating the N-terminus of a PST leads to increased solubility and activity. The truncated PSTs of the present invention are thus able to more efficiently conjugate sialic acid residues in an α-2,8 or an α-2,9 configuration as compared to an unmodified PST protein.

II. Definitions

The following abbreviations are used herein:

| | |
|---|---|
| Ara = | arabinosyl; |
| Fru = | fructosyl; |
| Fuc = | fucosyl; |
| Gal = | galactosyl; |
| GalNAc = | N-acetylgalactosaminyl; |
| Glc = | glucosyl; |
| GlcNAc = | N-acetylglucosaminyl; |
| Man = | mannosyl; and |
| NeuAc = | sialyl (N-acetylneuraminyl). |

An "acceptor substrate" or an "acceptor saccharide" for a glycosyltransferase, e.g., a poly-sialyltransferase protein, is an oligosaccharide moiety that can act as an acceptor for a particular glycosyltransferase. When the acceptor substrate is contacted with the corresponding glycosyltransferase and sugar donor substrate, and other necessary reaction mixture components, and the reaction mixture is incubated for a sufficient period of time, the glycosyltransferase transfers sugar residues from the sugar donor substrate to the acceptor substrate. The acceptor substrate can vary for different types of a particular glycosyltransferase. Accordingly, the term "acceptor substrate" is taken in context with the particular glycosyltransferase of interest for a particular application. Acceptor substrates for poly-sialyltransferase proteins, and additional glycosyltransferases, are described herein.

A "donor substrate" for glycosyltransferases is an activated nucleotide sugar. Such activated sugars generally consist of uridine, guanosine, and cytidine monophosphate derivatives of the sugars (UMP, GMP and CMP, respectively) or diphosphate derivatives of the sugars (UDP, GDP and CDP, respectively) in which the nucleoside monophosphate or diphosphate serves as a leaving group. Donor substrate for poly-sialyltransferase proteins include, e.g., activated sugar nucleotides comprising the desired sialic acid. For instance, in the case of NeuAc, the activated sugar is CMP-NeuAc. Bacterial, plant, and fungal systems can sometimes use other activated nucleotide sugars.

Oligosaccharides are considered to have a reducing end and a non-reducing end, whether or not the saccharide at the reducing end is in fact a reducing sugar. In accordance with accepted nomenclature, oligosaccharides are depicted herein with the non-reducing end on the left and the reducing end on the right. All oligosaccharides described herein are described with the name or abbreviation for the non-reducing saccharide (e.g., Gal), followed by the configuration of the glycosidic bond (α or β), the ring bond, the ring position of the reducing saccharide involved in the bond, and then the name or abbreviation of the reducing saccharide (e.g., GlcNAc). The linkage between two sugars may be expressed, for example, as 2,3, 2→3, or (2,3). Each saccharide is a pyranose or furanose.

As used herein, a "sialic acid moiety" refers to a molecule that includes sialic acid or that can be derived from sialic acid. Sialic acid moieties are usually monosaccharides, e.g., CMP-sialic acid.

As used herein, a "polymer of sialic acid moieties" refers to a multitude of conjugated sialic acid moieties, i.e., more than one. Such sialic acid polymers include homo-polymers of sialic acid that are all linked in the same configuration, e.g., a "homo-polymer of α-2,8-linked sialic acid moieties" or a "homo-polymer of α-2,9-linked sialic acid moieties." Sialic acid polymers also include a "co-polymer of α-2,8/α-2,9-linked sialic acid moieties." The linkage of the sialic acid polymers will depend on the identity of the poly-sialyltransferase included in the poly-sialyltransferase protein.

As used herein, a "polysialylated product or product saccharide" refers an oligosaccharide, a polysaccharide, or a carbohydrate moiety, either unconjugated or conjugated to a glycolipid or a glycoprotein, e.g., a biomolecule, that includes at least three sialic acid moieties. In preferred embodiments of a polysialylated product or product saccharide, a first single sialic acid moiety is conjugated to an acceptor substrate or biomolecule in an α-2,3 configuration; a second single sialic acid moiety is conjugated to the first single sialic acid moiety in an α-2,8 configuration; and one or more sialic acid moieties are conjugated to the second single sialic acid moiety. A polysialylated product or product saccharide comprises at least 3 sialic acid moieties. In other embodiments, a polysialylated product or product saccharide comprises at least 5, 7, 12, 25, 45, 80, 100, 150, 200, 250, or 500 sialic acid moieties. In further embodiments, a polysialylated product or product saccharide comprises at least between 3 and 12, 25, 45, 80, 100, 150, 200, 250, or 500 sialic acid moieties. In still further embodiments, a polysialylated product or product saccharide comprises up to 12, 25, 45, 80, 100, 150, 200, 250, or 500 sialic acid moieties.

In some embodiments other sugar moieties, e.g., fucose, galactose, GalNAc, glucose, or GlcNAc, are also added to the acceptor substrate through the action of additional glycosyltransferases to produce the poly-sialylated product saccharide. In some embodiments, the acceptor substrate comprises a galactose moiety and a bi-functional sialyltransferase protein is used to add a first single sialic acid moiety to the galactose moiety in an α-2,3 configuration; the poly-sialyltransferase can then add a second single sialic acid moiety in an α-2,8 configuration to the first sialic acid moiety; and add one or more sialic acid moieties to the second single sialic acid moiety, making the poly-sialylated product saccharide. In other embodiments, the acceptor substrate comprises a first sialic acid moiety in an α-2,3 configuration and poly-sialyltransferase protein is used to a second single sialic acid moiety in an α-2,8 configuration to the first sialic acid moiety; and to add one or more sialic acid moieties to the second single sialic acid moiety, making the poly-sialylated product saccharide. In a further embodiment, the acceptor substrate comprises a first sialic acid moiety in an α-2,3 configuration conjugated to a second single sialic acid moiety in an α-2,8 configuration to the first sialic acid moiety; and the poly-sialyltransferase protein is used to add one or more sialic acid moieties to the second single sialic acid moiety, making the poly-sialylated product saccharide.

The term "sialic acid" or "sialic acid moiety" refers to any member of a family of nine-carbon carboxylated sugars. The most common member of the sialic acid family is N-acetyl-neuraminic acid (2-keto-5-acetamido-3,5-dideoxy-D-glycero-D-galactononulopyranos-1-onic acid (often abbreviated as Neu5Ac, NeuAc, or NANA). A second member of the family is N-glycolyl-neuraminic acid (Neu5Gc or NeuGc), in which the N-acetyl group of NeuAc is hydroxylated. A third sialic acid family member is 2-keto-3-deoxy-nonulosonic acid (KDN) (Nadano et al. (1986) *J. Biol. Chem.* 261: 11550-11557; Kanamori et al., *J. Biol. Chem.* 265: 21811-21819 (1990)). Also included are 9-substituted sialic acids such as a 9-O—$C_1$-$C_6$ acyl-Neu5Ac like 9-O-lactyl-Neu5Ac or 9-O-acetyl-Neu5Ac, 9-deoxy-9-fluoro-Neu5Ac and 9-azido-9-deoxy-Neu5Ac. For review of the sialic acid family, see, e.g., Varki, *Glycobiology* 2: 25-40 (1992); *Sialic Acids: Chemistry, Metabolism and Function*, R. Schauer, Ed. (Springer-Verlag, New York (1992)). The synthesis and use of sialic acid compounds in a sialylation procedure is disclosed in international application WO 92/16640, published Oct. 1, 1992.

Much of the nomenclature and general laboratory procedures required in this application can be found in Sambrook, et al., *Molecular Cloning: A Laboratory Manual* (2nd Ed.), Vol. 1-3, Cold Spring Harbor Laboratory, Cold Spring Harbor, N.Y., 1989. The manual is hereinafter referred to as "Sambrook et al."

The terms "sialyltransferase" or a nucleic acid encoding a "sialyltransferase" refer to nucleic acids and polypeptide polymorphic variants, alleles, mutants, and interspecies homologs that are capable of catalyzing the transfer of a first sialic acid molecule to an acceptor substrate. Bacterial and mammalian sialyltransferases are known. Sialic acid residues can be conjugated to an acceptor molecule using a variety of linkages, e.g., α-2,3, α-2,6, and α-2,8. Sialyltransferases can have one or more activities. Many sialyltransferases are mono-functional. As an example, CST-I and CST-III are mono-functional sialyltransferases from *Campylobacter jejuni*, that catalyze transfer of sialic acid in an α-2,3 linkage. See, e.g., U.S. Pat. Nos. 6,689,604 and 6,699,705. Other exemplary mono-functional sialyltransferases are from *Neisseria*, e.g., sialyltransferases disclosed in U.S. Pat. No. 6,096,529.

Other sialyltransferases have more than one enzymatic activity, i.e., add sialic acid to a substrate in more than one linkage. For example, CST-II enzymes from *C. jejuni* add sialic acid to an acceptor molecule using at least one of the following linkages: α-2,3 or α-2,8. Some CST-II enzymes add multiple sialic acids to an acceptor molecule in the α-2,8 configuration. CST-II enzyme activities from different *C. jejuni* strains can differ. Various CST-II enzymes, nucleic acids and activity assays are disclosed in, e.g., U.S. Pat. No. 6,699,705; Gilbert et al., *J Biol Chem.* 277:327-37 (2002); and Gilbert et al., *J Biol Chem.* 275:3896-906 (2000). A multi-functional sialyltransferase from *Haemophilus* has also been described. See, e.g., Fox et al., *J Biol Chem.* 281:40024-32 (2006).

The term "poly-sialyltransferase" or "PST" and polypeptide polymorphic variants, alleles, mutants, and interspecies homologs that: (1) have an amino acid sequence that has at least 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of over a region of at least about 25, 50, 100, 200, 500, 1000, or more amino acids, to an amino acid sequence encoded by a poly-sialyltransferase nucleic acid or to an amino acid sequence of a poly-sialyltransferase protein (for exemplary poly-sialyltransferase protein sequences, see, e.g., SEQ ID NO:1) and (2) bind to antibodies, e.g., polyclonal antibodies, raised against an immunogen comprising an amino acid sequence of a poly-sialyltransferase protein, and conservatively modified variants thereof. The active domain of a PST has at least 90%, preferably at least 91%, 92%, 93%, 94%, 95%, 96%, 97%, 98%, 99% amino acid identity to a poly-sialyltransferase active domain of, e.g., SEQ ID NO: 1. A polynucleotide or polypeptide sequence is typically from a bacteria including, but not limited to *Neisseria, Campylobacter, Haemophilus, Mannheimia* and *Pasteurella*. The nucleic acids and proteins of the invention include both naturally occurring or recombinant molecules. A poly-sialyltransferase protein typically has poly-sialyltransferase activity, including e.g., activity to make α-2,8 linkages, α-2,9 linkages or α-2,8/α-2,9 linkages. Poly-sialyltransferase assays can be performed according to methods known to those of skill in the art, using appropriate donor substrates and acceptor substrates, as described herein. Typically, a PST enzyme adds multiple sialic acid residues to a sialic acid residue previously conjugated to an acceptor substrate.

As used herein, a "truncated PST polypeptide" or grammatical variants, refers to a PST polypeptide that has been manipulated to remove at least one amino acid residue, relative to a wild-type PST polypeptide that occurs in nature, so long as the truncated PST polypeptide retains enzymatic activity. Examples of wild-type or naturally occurring PST proteins include, e.g., SEQ ID NO:1. Preferred PST truncations are 19 or 32 amino acid deletions from the N-terminus of SEQ ID NO:1. Other preferred examples of truncated PST proteins are SEQ ID NOs:3 and 5 or amino acid sequences with at least 80%, 85%, 90%, preferably 91%, 92%, 93%, 94%, 95%, 96%, 97%, 98% or 99% or greater amino acid sequence identity to SEQ ID NO:3 or SEQ ID NO:5. In a further preferred embodiment, the truncated PST proteins is fused to, e.g., a Mal-E protein or a sialyltransferase.

A "fusion PST polypeptide" or a "fusion poly-sialyltransferase polypeptide" of the invention is a polypeptide that contains an active PST domain. The fusion polypeptide is capable of catalyzing the polysialyl transfer reaction. Typically, the catalytic domains of the fusion polypeptides will be at least substantially identical to those of PSTs and fusion proteins from which the catalytic domains are derived. In some embodiments, a recombinant protein that is a fusion of a poly-sialyltransferase and a sialyltransferase can be constructed to create a "self-priming PST". In some embodiments, the self-priming poly-sialyltransferase protein is able to conjugate a first single sialic acid moiety to a non-sialic acid sugar residue in acceptor substrate through the activity of sialyltransferase, typically in an α-2,3 configuration. In a further embodiment, the self-priming poly-sialyltransferase protein also conjugates a second single sialic acid moiety to previously added first single sialic acid moiety through the activity of multi-functional sialyltransferase, typically in an α-2,8 configuration. In another embodiment, the self-priming poly-sialyltransferase protein add a sialic acid residue to an acceptor substrate that had been previously sialylated using an α-2,3 configuration. Once an appropriate number of sialic acid residues are added to the acceptor substrate to "prime" the polysialyltransferase activity, the self-priming poly-sialyltransferase protein can then conjugate one or more sialic acid moieties to a sialic acid moiety through the activity of the poly-sialyltransferase. In some embodiments, the activity of the poly-sialyltransferase produces a polymer of sialic acid moieties.

The recombinant proteins of the invention can be constructed and expressed as a fusion protein with a molecular "purification tag" at one end, which facilitates purification or identification of the protein. Such tags can also be used for immobilization of a protein of interest during the glycosylation reaction. Suitable tags include "epitope tags," which are a protein sequence that is specifically recognized by an antibody. Epitope tags are generally incorporated into fusion proteins to enable the use of a readily available antibody to unambiguously detect or isolate the fusion protein. A "FLAG tag" is a commonly used epitope tag, specifically recognized by a monoclonal anti-FLAG antibody, consisting of the sequence AspTyrLysAspAspAsp AspLys [SEQ ID NO: 7] or a substantially identical variant thereof. Other suitable tags are known to those of skill in the art, and include, for example, an affinity tag such as a hexahistidine peptide, which will bind to metal ions such as nickel or cobalt ions or a myc tag. Proteins comprising purification tags can be purified using a binding partner that binds the purification tag, e.g., antibodies to the purification tag, nickel or cobalt ions or resins, and amylose, maltose, or a cyclodextrin. Purification tags also include maltose binding domains and starch binding domains. Purification of maltose binding domain proteins is known to those of skill in the art. Starch binding domains are described in WO99/15636, herein incorporated by reference. Affinity purification of a fusion protein comprising a starch binding domain using a beta-cylodextrin (BCD)-derivatized resin is described in WO 2005/014779, published Feb. 17, 2005, herein incorporated by reference in its entirety.

An "accessory enzyme," as referred to herein, is an enzyme that is involved in catalyzing a reaction that, for example, forms a nucleotide sugar for a poly-sialyltransferase reaction, e.g., a sialic acid synthase.

A "catalytic domain" or "active domain" refers to a portion of an enzyme that is sufficient to catalyze an enzymatic reaction that is normally carried out by the enzyme. For example, a catalytic domain of a PST polypeptide will include a sufficient portion of the PST to catalyze a transfer of a sialic acid to a substrate. A catalytic domain can include an entire enzyme, a subsequence thereof, or can include additional amino acid sequences that are not attached to the enzyme or subsequence as found in nature.

"Commercial scale" refers to gram scale production of a poly-sialylated product in a single reaction. In preferred embodiments, commercial scale refers to production of greater than about 50, 75, 80, 90, 100, 125, 150, 175, or 200 grams of poly-sialylated product.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

Those of skill recognize that many amino acids can be substituted for one another in a protein without affecting the function of the protein, i.e., a conservative substitution can be the basis of a conservatively modified variant of a protein such as the disclosed poly-sialyltransferase proteins and derivatives thereof. An incomplete list of conservative amino acid substitutions follows. The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V), Alanine (A); 6) Phenylalanine (F), Tyrosine (Y), Tryptophan (W); 7) Serine (S), Threonine (T), Cysteine (C); and 8) Cysteine (C), Methionine (M) (see, e.g., Creighton, *Proteins* (1984)).

The cells and methods of the invention are useful for producing a poly-sialylated product, generally by transferring a sialic acid moiety from a donor substrate to an acceptor molecule. The cells and methods of the invention are also useful for producing a poly-sialylated product sugar comprising additional sugar residues, generally by transferring a additional monosaccharide or a sulfate groups from a donor substrate to an acceptor molecule. The addition generally takes place at the non-reducing end of an oligosaccharide, polysaccharide (e.g., heparin, carragenin, and the like) or a carbohydrate moiety on a glycolipid or glycoprotein, e.g., a biomolecule. Biomolecules as defined here include but are not limited to biologically significant molecules such as carbohydrates, oligosaccharides, peptides (e.g., glycopeptides), proteins (e.g., glycoproteins), and lipids (e.g., glycolipids, phospholipids, sphingolipids and gangliosides).

The term "nucleic acid" refers to a deoxyribonucleotide or ribonucleotide polymer in either single- or double-stranded form, and unless otherwise limited, encompasses known analogues of natural nucleotides that hybridize to nucleic acids in manner similar to naturally occurring nucleotides. Unless otherwise indicated, a particular nucleic acid sequence includes the complementary sequence thereof. The terms "nucleic acid", "nucleic acid sequence", and "polynucleotide" are used interchangeably herein.

The term "operably linked" refers to functional linkage between a nucleic acid expression control sequence (such as a promoter, signal sequence, or array of transcription factor binding sites) and a second nucleic acid sequence, wherein the expression control sequence affects transcription and/or translation of the nucleic acid corresponding to the second sequence.

The term "recombinant" when used with reference to a cell indicates that the cell replicates a heterologous nucleic acid, or expresses a peptide or protein encoded by a heterologous nucleic acid. Recombinant cells can contain genes that are not found within the native (non-recombinant) form of the cell. Recombinant cells can also contain genes found in the native form of the cell wherein the genes are modified and re-introduced into the cell by artificial means. The term also encompasses cells that contain a nucleic acid endogenous to the cell that has been modified without removing the nucleic acid from the cell; such modifications include those obtained by gene replacement, site-specific mutation, and related techniques.

A "recombinant nucleic acid" refers to a nucleic acid that was artificially constructed (e.g., formed by linking two naturally-occurring or synthetic nucleic acid fragments). This term also applies to nucleic acids that are produced by replication or transcription of a nucleic acid that was artificially constructed. A "recombinant polypeptide" is expressed by transcription of a recombinant nucleic acid (i.e., a nucleic acid that is not native to the cell or that has been modified from its naturally occurring form), followed by translation of the resulting transcript.

A "heterologous polynucleotide" or a "heterologous nucleic acid", as used herein, is one that originates from a source foreign to the particular host cell, or, if from the same source, is modified from its original form. Thus, a heterologous poly-sialyltransferase gene in a prokaryotic host cell includes a poly-sialyltransferase gene that is endogenous to the particular host cell but has been modified. Modification of the heterologous sequence may occur, e.g., by treating the DNA with a restriction enzyme to generate a DNA fragment that is capable of being operably linked to a promoter. Techniques such as site-directed mutagenesis are also useful for modifying a heterologous sequence.

A "subsequence" refers to a sequence of nucleic acids or amino acids that comprise a part of a longer sequence of nucleic acids or amino acids (e.g., polypeptide) respectively.

A "recombinant expression cassette" or simply an "expression cassette" is a nucleic acid construct, generated recombinantly or synthetically, with nucleic acid elements that are capable of affecting expression of a structural gene in hosts compatible with such sequences. Expression cassettes include at least promoters and optionally, transcription termination signals. Typically, the recombinant expression cassette includes a nucleic acid to be transcribed (e.g., a nucleic acid encoding a desired polypeptide), and a promoter. Additional factors necessary or helpful in effecting expression may also be used as described herein. For example, an expression cassette can also include nucleotide sequences that encode a signal sequence that directs secretion of an expressed protein from the host cell. Transcription termination signals, enhancers, and other nucleic acid sequences that influence gene expression, can also be included in an expression cassette.

The term "isolated" refers to material that is substantially or essentially free from components which interfere with the activity of an enzyme. For cells, saccharides, nucleic acids, and polypeptides of the invention, the term "isolated" refers to material that is substantially or essentially free from components which normally accompany the material as found in its native state. Typically, isolated saccharides, proteins or nucleic acids of the invention are at least about 50%, 55%, 60%, 65%, 70%, 75%, 80% or 85% pure, usually at least about 90%, 91%, 92%, 93%, 94%, 95%, 96%, 97%, 98%, or 99% pure as measured by band intensity on a silver stained gel or other method for determining purity. Purity or homogeneity can be indicated by a number of means well known in the art, such as polyacrylamide gel electrophoresis of a protein or nucleic acid sample, followed by visualization upon staining. For certain purposes high resolution will be needed and HPLC or a similar means for purification utilized. For oligonucleotides, or other galactosylated products, purity can be determined using, e.g., thin layer chromatography, HPLC, or mass spectroscopy.

The terms "identical" or percent "identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the following sequence comparison algorithms or by visual inspection.

The phrase "substantially identical," in the context of two nucleic acids or polypeptides, refers to two or more sequences or subsequences that have at least 60%, preferably 80% or 85%, most preferably at least 90%, 91%, 92%, 93%, 94%, 95%, 96%, 97%, 98%, or 99% nucleotide or amino acid residue identity, when compared and aligned for maximum correspondence, as measured using one of the following sequence comparison algorithms or by visual inspection. Preferably, the substantial identity exists over a region of the sequences that is at least about 50 residues in length, more preferably over a region of at least about 100 residues, and most preferably the sequences are substantially identical over at least about 150 residues. In a most preferred embodiment, the sequences are substantially identical over the entire length of the coding regions.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, *Current Protocols in Molecular Biology*, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) *J. Mol. Biol.* 215: 403-410 and Altschuel et al. (1977) *Nucleic Acids Res.* 25: 3389-3402, respectively. Software for performing BLAST analyses is publicly available through the National Center for Biotechnology Information (www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89:10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions, as described below.

The phrase "hybridizing specifically to", refers to the binding, duplexing, or hybridizing of a molecule only to a particular nucleotide sequence under stringent conditions when that sequence is present in a complex mixture (e.g., total cellular) DNA or RNA.

The term "stringent conditions" refers to conditions under which a probe will hybridize to its target subsequence, but to no other sequences. Stringent conditions are sequence-dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength, pH, and nucleic acid concentration) at which 50% of the probes complementary to the target sequence hybridize to the target sequence at equilibrium. (As the target sequences are generally present in excess, at Tm, 50% of the probes are occupied at equilibrium). Typically, stringent conditions will be those in which the salt concentration is less than about 1.0 M $Na^+$ ion, typically about 0.01 to 1.0 M $Na^+$ ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions can also be achieved with the addition of destabilizing agents such as formamide. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90-95° C. for 30-120 sec, an annealing phase lasting 30-120 sec, and an extension phase of about 72° C. for 1-2 min. Protocols and guidelines for low and high stringency amplification reactions are available, e.g., in Innis, et al. (1990) *PCR Protocols: A Guide to Methods and Applications* Academic Press, N.Y.

The phrases "specifically binds to" or "specifically immunoreactive with", when referring to an antibody refers to a binding reaction which is determinative of the presence of the protein or other antigen in the presence of a heterogeneous population of proteins, saccharides, and other biologics. Thus, under designated immunoassay conditions, the specified antibodies bind preferentially to a particular antigen and do not bind in a significant amount to other molecules present in the sample. Specific binding to an antigen under such conditions requires an antibody that is selected for its specificity for a particular antigen. A variety of immunoassay formats can be used to select antibodies specifically immunoreactive with a particular antigen. For example, solid-phase ELISA immunoassays are routinely used to select monoclonal antibodies specifically immunoreactive with an antigen. See Harlow and Lane (1988) *Antibodies, A Laboratory Manual*, Cold Spring Harbor Publications, New York, for a description of immunoassay formats and conditions that can be used to determine specific immunoreactivity.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. In a preferred embodiment, antibodies that specifically bind to a self-priming poly-sialyltransferae protein are produced. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce $F(ab)'_2$, a dimer of Fab which itself is a light chain joined to $V_H$-$C_H1$ by a disulfide bond. The $F(ab)'_2$ may be reduced under mild conditions to break the disulfide linkage in the hinge region, thereby converting the $F(ab)'_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990)).

For preparation of antibodies, e.g., recombinant, monoclonal, or polyclonal antibodies, many technique known in the art can be used (see, e.g., Kohler & Milstein, *Nature* 256:495-497 (1975); Kozbor et al., *Immunology Today* 4: 72 (1983); Cole et al., pp. 77-96 in *Monoclonal Antibodies and Cancer Therapy*, Alan R. Liss, Inc. (1985); Coligan, *Current Protocols in Immunology* (1991); Harlow & Lane, *Antibodies, A Laboratory Manual* (1988); and Goding, *Monoclonal Antibodies: Principles and Practice* (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, *Immunology* ($3^{rd}$ ed. 1997)). Techniques for the production of single chain antibodies or recombinant antibodies (U.S. Pat. Nos. 4,946,778, 4,816,567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545,806; 5,569,825; 5,625,126; 5,633,425; 5,661,016, Marks et al., *Bio/Technology* 10:779-783 (1992); Lonberg et al., *Nature* 368:856-859 (1994); Morrison, *Nature* 368:812-13 (1994); Fishwild et al., *Nature Biotechnology* 14:845-51 (1996); Neuberger, *Nature Biotechnology* 14:826 (1996); and Lonberg & Huszar, *Intern. Rev. Immunol.* 13:65-93 (1995)). Alternatively, phage display technology can be used to identify antibodies and heteromeric Fab fragments that specifically bind to selected antigens (see, e.g., McCafferty et al., *Nature* 348:552-554 (1990); Marks et al., *Biotechnology* 10:779-783 (1992)). Antibodies can also be made bispecific, i.e., able to recognize two different antigens (see, e.g., WO 93/08829, Traunecker et al., *EMBO J.* 10:3655-3659 (1991); and Suresh et al., *Methods in Enzymology* 121:210 (1986)). Antibodies can also be heteroconjugates, e.g., two covalently joined antibodies, or immunotoxins (see, e.g., U.S. Pat. No. 4,676,980, WO 91/00360; WO 92/200373; and EP 03089).

In one embodiment, the antibody is conjugated to an "effector" moiety. The effector moiety can be any number of molecules, including labeling moieties such as radioactive labels or fluorescent labels for use in diagnostic assays.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies raised to IgE protein, polymorphic variants, alleles, orthologs, and conservatively modified variants, or splice variants, or portions thereof, can be selected to obtain only those polyclonal antibodies that are specifically immunoreactive with IgE proteins and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988) for a description of immunoassay formats and conditions that can be used to determine specific immunoreactivity).

An "antigen" is a molecule that is recognized and bound by an antibody, e.g., peptides, carbohydrates, organic molecules, or more complex molecules such as glycolipids and glycoproteins. The part of the antigen that is the target of antibody binding is an antigenic determinant and a small functional group that corresponds to a single antigenic determinant is called a hapten.

A "label" is a composition detectable by spectroscopic, photochemical, biochemical, immunochemical, or chemical means. For example, useful labels include $^{32}P$, $^{125}I$, fluorescent dyes, electron-dense reagents, enzymes (e.g., as commonly used in an ELISA), biotin, digoxigenin, or haptens and proteins for which antisera or monoclonal antibodies are available (e.g., the polypeptide of SEQ ID NO:2 can be made detectable, e.g., by incorporating a radiolabel into the peptide, and used to detect antibodies specifically reactive with the peptide).

The term "immunoassay" is an assay that uses an antibody to specifically bind an antigen. The immunoassay is characterized by the use of specific binding properties of a particular antibody to isolate, target, and/or quantify the antigen.

The term "carrier molecule" means an immunogenic molecule containing antigenic determinants recognized by T cells. A carrier molecule can be a protein or can be a lipid. A carrier protein is conjugated to a polypeptide to render the polypeptide immunogenic. Carrier proteins include keyhole limpet hemocyanin, horseshoe crab hemocyanin, and bovine serum albumin.

The term "adjuvant" means a substance that nonspecifically enhances the immune response to an antigen. Adjuvants include Freund's adjuvant, either complete or incomplete; Titermax gold adjuvant; alum; and bacterial LPS.

The term "contacting" is used herein interchangeably with the following: combined with, added to, mixed with, passed over, incubated with, flowed over, etc.

III. Sialyltransferases

Polysialyltransferases are enzymes capable of adding sialic acid residues to an acceptor substrate. Typically, polysialyltransferases add sialic acid residues to a "primed substrate", i.e., a substrate with a sialic acid residues linked to its substrate. Additional sialyltransferases can be used to add appropriate sialic acid residues and "prime" the acceptor substrate for activity of the PST.

A. PST polypeptides

PST proteins have previously been identified and are thus, identifiable by those of skill in the art. For example, a PST can be aligned with the consensus sequence of pfam07388, α-2-8-polyST, α-2,8-polysialyltransferase. See, e.g., Marchler-Bauer et al., *Nucleic Acids Res.* 33: D192-6 (2005). Other PST proteins that show alignment to the pfam07388 can be used in the invention. The α-2-8-polyST, α-2,8-polysialyltransferase family of proteins is a group of proteins that were identified as such based on sequence comparisons. See, e.g., Steenbergen and Vimr, *J Biol Chem.* 278:15349-15359 (2003). In other embodiments, the truncated PST proteins comprise a sequence from PST protein that is a member of CAZy family GT38. See, e.g., Coutinho, P.M. & Henrissat, B. (1999) Carbohydrate-Active Enzymes server at URL: afmb-.cnrs-mrs.fr/CAZY/. PST proteins include proteins that synthesize homo-polymers of α2,8-linked sialic acid residues, homo-polymers of α2,9-linked sialic acid residues, or co-polymers of α2,8/α2,9-linked sialic acid residues.

Exemplary PST proteins can be isolated from, e.g., *N. meningitidis* or *E. coli* bacteria. The proteins for these PST are both from the glycosyltransferase family GT-38, which contains only bacterial members. See, e.g., Coutinho, P. M. et al., *Journal of Molecular Biology*, 328:307-317 (2003). Although the exemplified *N. meningitidis* and *E. coli* proteins make identical structures in vivo, the two protein share 33% identity.

B. Sialyltransferases

Some sialyltransferase proteins have at least one of α-2,3 and α-2,8 sialyltransferase activities. Examples are disclosed in e.g., U.S. Pat. Nos. 6,503,744 and 6,699,705, which are herein incorporated by reference for all purposes. Such sialyltransferase proteins are members of CAZy family 42. See, e.g., Coutinho, P.M. & Henrissat, B. (1999) Carbohydrate-Active Enzymes server at URL: afmb.cnrs-mrs.fr/CAZY/. these bacterial sialyltransferase polypeptides comprise two motifs: sialyltransferase motif A, DVFRCNQFYFED/E [SEQ ID NO: 8], and conservatively modified variants of that sequence and sialyltransferase motif B, RITSGVYMC [SEQ ID NO: 9], and conservatively modified variants of that sequence. In some embodiments, the sialyltransferase polypeptides comprise either the sialyltransferase motif A DVFRCNQFYFED [SEQ ID NO: 8] or DVFRCNQFYFEE [SEQ ID NO: 8], and sialyltransferase motif B RITSGVYMC [SEQ ID NO: 9]. See, e.g., PCT/CA2005/001432, which is herein incorporated by reference for all purposes. The conserved sialyltransferase motifs were identified by analysis of multiple bacterial sialyltransferases. The amino acid sequence of 18 sialyltransferases were aligned, and the conserved sialyltransferase sequence motifs A and B were identified by visual inspection.

An exemplary sialyltransferase is a CstII protein from *C. jejuni*. Members of this family of sialyltransferase proteins or nucleic acids can be isolated from the following *C. jejuni* strains: OH4384, GenBank accession number AR271700; OH4382; O:10, GenBank accession number AR271701; O:23, GenBank accession number AF401529; O:41, GenBank accession number AR271702; and HB93-13, GenBank accession number AY297047. See also, e.g., U.S. Pat. Nos. 6,503,744 and 6,699,705, which are herein incorporated by reference for all purposes In some embodiments the sialyltransferase polypeptides also comprise other amino acid residues that appear to be important for enzymatic activity. For example, the structure of Cst-II from *Campylobacter jejuni* strain OH4384 has been solved. (See, e.g., Chiu et al., *Nat. Struc. Mol. Biol.* 11:163-170 (2004)). Mutational analysis of the Cst-II enzyme demonstrated that, for example the arginine residue of sialyltransferase motif B is required for activity. Residues numbers are listed for the OH4384 protein; corresponding residues for other Cst-II proteins can be determined using sequence alignments. See, e.g., PCT/CA2005/001432, which is herein incorporated by reference for all purposes. The arginine residue of sialyltransferase motif B is referred to as R129 in Cst-II and correlates to R165 of the sialyltransferase consensus sequence of FIG. 1. Other amino acid residues that appear to be important for catalytic activity include Cst-II Y156, Cst-II Y162 and Cst-II H188. Other amino acids that affect protein activity are discussed in PCT/CA2005/001432.

IV. Isolation of Nucleic Acids Encoding PST Polypeptides

Nucleic acids that encode PST polypeptides include nucleic acids that encode the full-length, naturally occurring PST polypeptides described above and enzymatically active truncations of those sequences. The PST polypeptides of the invention catalyze the transfer of a sialic acid moiety from a donor substrate to an acceptor substrate and assays to measure that activity are disclosed herein.

Nucleic acids that encode additional PST polypeptides based on the information disclosed herein, and methods of obtaining such nucleic acids, are known to those of skill in the art. Suitable nucleic acids (e.g., cDNA, genomic, or subsequences (probes)) can be cloned, or amplified by in vitro methods such as the polymerase chain reaction (PCR), the ligase chain reaction (LCR), the transcription-based amplification system (TAS), or the self-sustained sequence replication system (SSR). A wide variety of cloning and in vitro amplification methodologies are well-known to persons of skill. Examples of these techniques and instructions sufficient to direct persons of skill through many cloning exercises are found in Berger and Kimmel, *Guide to Molecular Cloning Techniques, Methods in Enzymology* 152 Academic Press, Inc., San Diego, Calif. (Berger); Sambrook et al. (1989) *Molecular Cloning—A Laboratory Manual* (2nd ed.) Vol. 1-3, Cold Spring Harbor Laboratory, Cold Spring Harbor Press, NY, (Sambrook et al.); *Current Protocols in Molecular Biology*, F. M. Ausubel et al., eds., Current Protocols, a joint venture between Greene Publishing Associates, Inc. and John Wiley & Sons, Inc., (1994 Supplement) (Ausubel); Cashion et al., U.S. Pat. No. 5,017,478; and Carr, European Patent No. 0,246,864.

Standard molecular biology methods, e.g., PCR, can be used to generate truncations of any known PST sequence.

A DNA that encodes a PST polypeptide, or a subsequence or truncation thereof, can be prepared by any suitable method described above, including, for example, cloning and restriction of appropriate sequences with restriction enzymes. In one embodiment, nucleic acids encoding PST polypeptides are isolated by routine cloning methods. A nucleotide sequence encoding a poly-sialyltransferase polypeptide is, for example, a nucleic acid sequence coding for the PST of SEQ ID NO:1. Nucleic acid sequences can be used to provide probes that specifically hybridize to a gene encoding a PST polypeptide in a genomic DNA sample; or to an mRNA, encoding a PST polypeptide in a total RNA sample (e.g., in a Southern or Northern blot). Once the target nucleic acid encoding a PST polypeptide is identified, it can be isolated according to standard methods known to those of skill in the art (see, e.g., Sambrook et al. (1989) *Molecular Cloning: A Laboratory Manual, 2nd Ed., Vols.* 1-3, Cold Spring Harbor Laboratory; Berger and Kimmel (1987) *Methods in Enzymology, Vol.* 152*: Guide to Molecular Cloning Techniques*, San Diego: Academic Press, Inc.; or Ausubel et al. (1987) *Current Protocols in Molecular Biology*, Greene Publishing and Wiley-Interscience, New York). Further, the isolated nucleic acids can be cleaved with restriction enzymes to create nucleic acids encoding the full-length a PST polypeptide, or subsequences or truncation variants thereof, e.g., truncations containing subsequences encoding at least a subsequence of a catalytic domain of a PST polypeptide. These restriction enzyme fragments, encoding a PST polypeptide or subsequences thereof, may then be ligated.

A nucleic acid encoding a PST polypeptide, or a subsequence thereof, can be characterized by assaying for the expressed product. Assays based on the detection of the physical, chemical, or immunological properties of the expressed protein can be used. For example, one can identify a cloned PST polypeptide, by the ability of a protein encoded by the nucleic acid to catalyze the transfer of a sialic acid moiety from a donor substrate to an appropriate acceptor substrate. In one method, capillary electrophoresis is employed to detect the reaction products. This highly sensitive assay involves using either saccharide or disaccharide aminophenyl derivatives which are labeled with fluorescein as described in Wakarchuk et al. (1996) *J. Biol. Chem.* 271 (45): 28271-276. To assay for poly-sialyltransferase activity, Lac-FCHASE, Gal-β-1,3-GalNAc-α-FCHASE (T-Ag-FCHASE), or NeuAc-α-2,3-Gal-β-1,3-GalNAc-α-FCHASE can be used as a substrate. See, e.g., U.S. Pat. No. 6,503,744, which is herein incorporated by reference. In some embodiments, the reaction can be primed by using an additional sialyltransferase. Other methods for detection of oligosaccharide reaction products include thin layer chromatography and GC/MS and are disclosed in U.S. Pat. No. 6,503,744, which is herein incorporated by reference.

Also, a nucleic acid encoding a PST polypeptide, or a subsequence thereof, can be chemically synthesized. Suitable methods include the phosphotriester method of Narang et al. (1979) *Meth. Enzymol.* 68: 90-99; the phosphodiester method of Brown et al. (1979) *Meth. Enzymol.* 68: 109-151; the diethylphosphoramidite method of Beaucage et al. (1981) *Tetra. Lett.,* 22: 1859-1862; and the solid support method of U.S. Pat. No. 4,458,066. Chemical synthesis produces a single stranded oligonucleotide. This can be converted into double stranded DNA by hybridization with a complementary sequence, or by polymerization with a DNA polymerase using the single strand as a template. One of skill recognizes that while chemical synthesis of DNA is often limited to sequences of about 100 bases, longer sequences may be obtained by the ligation of shorter sequences.

Nucleic acids encoding PST polypeptides, or subsequences thereof, can be cloned using DNA amplification methods such as polymerase chain reaction (PCR). Thus, for example, the nucleic acid sequence or subsequence is PCR amplified, using a sense primer containing one restriction enzyme site (e.g., NdeI) and an antisense primer containing another restriction enzyme site (e.g., HindIII). This will produce a nucleic acid encoding the desired PST polypeptide or a subsequence and having terminal restriction enzyme sites. This nucleic acid can then be easily ligated into an expression vector having the appropriate corresponding restriction enzyme sites. Suitable PCR primers can be determined by one of skill in the art using the sequence information provided in GenBank or other sources. Appropriate restriction enzyme sites can also be added to the nucleic acid encoding the PST polypeptide or a protein subsequence thereof by site-directed mutagenesis. The plasmid containing the PST polypeptide-encoding nucleotide sequence or subsequence is cleaved with the appropriate restriction endonuclease and then ligated into an appropriate vector for amplification and/or expression according to standard methods. Examples of techniques sufficient to direct persons of skill through in vitro amplification methods are found in Berger, Sambrook, and Ausubel, as well as Mullis et al., (1987) U.S. Pat. No. 4,683,202; *PCR Protocols A Guide to Methods and Applications* (Innis et al., eds) Academic Press Inc. San Diego, Calif. (1990) (Innis); Arnheim & Levinson (Oct. 1, 1990) *C&EN* 36-47; *The Journal Of NIH Research* (1991) 3: 81-94; (Kwoh et al. (1989) *Proc. Natl. Acad. Sci. USA* 86: 1173; Guatelli et al. (1990) *Proc. Natl. Acad. Sci. USA* 87, 1874; Lomell et al. (1989) *J. Clin. Chem.,* 35: 1826; Landegren et al., (1988) *Science* 241: 1077-1080; Van Brunt (1990) *Biotechnology* 8: 291-294; Wu and Wallace (1989) *Gene* 4: 560; and Barringer et al. (1990) *Gene* 89: 117.

PST proteins can be isolated by amplifying an appropriate DNA sequence, for example, a DNA sequence for a bacterial chromosome. Examples of PCR primers that can be used to amplify nucleic acids encoding a PST protein include the following primer pairs, e.g., primers for amplifying *E. coli* PST:

```
                                         [SEQ ID NO: 10]
5'- AAGGTATAAGACATATGATATTTGATGCTAGTTTAAAGAAG
and

[SEQ ID NO: 11]
3'- CCTAGGTCGACTTACTCCCCCAAGAAAATCCTTTTATCGTGC.
```

Other physical properties of a recombinant PST polypeptide expressed from a particular nucleic acid, can be compared to properties of known PST polypeptides to provide another method of identifying suitable sequences or domains of the PST polypeptide that are determinants of acceptor substrate specificity and/or catalytic activity. Alternatively, a putative PST polypeptide can be mutated, and its role as a PST, or the role of particular sequences or domains established by detecting a variation in the structure of a carbohydrate normally produced by the unmutated, naturally-occurring, or control PST polypeptide. Those of skill will recognize that mutation or modification of PST polypeptide of the invention can be facilitated by molecular biology techniques to manipulate the nucleic acids encoding the bi-functional sialyltransferase polypeptide or PST polypeptide, e.g., PCR.

V. Expressing PST Polypeptides in Host Cells

PST proteins of the invention can be expressed in a variety of host cells, including *E. coli*, other bacterial hosts, and yeast. The host cells are preferably microorganisms, such as, for example, yeast cells, bacterial cells, or filamentous fungal cells. Examples of suitable host cells include, for example, *Azotobacter* sp. (e.g., *A. vinelandii*), *Pseudomonas* sp., *Rhizobium* sp., *Erwinia* sp., *Escherichia* sp. (e.g., *E. coli*), *Bacillus, Pseudomonas, Proteus, Salmonella, Serratia, Shigella, Rhizobia, Vitreoscilla, Paracoccus* and *Klebsiella* sp., among many others. The cells can be of any of several genera, including *Saccharomyces* (e.g., *S. cerevisiae*), *Candida* (e.g., *C. utilis, C. parapsilosis, C. krusei, C. versatilis, C. lipolytica, C. zeylanoides, C. guilliermondii, C. albicans*, and *C. humicola*), *Pichia* (e.g., *P. farinosa* and *P. ohmeri*), *Torulopsis* (e.g., *T. candida, T. sphaerica, T. xylinus, T. famata*, and *T. versatilis*), Debaryomyces (e.g., *D. subglobosus, D. cantarellii, D. globosus, D. hansenii*, and *D. japonicus*), *Zygosaccharomyces* (e.g., *Z. rouxii* and *Z. bailii*), *Kluyveromyces* (e.g., *K. marxianus*), *Hansenula* (e.g., *H. anomala* and *H. jadinii*), and Brettanomyces (e.g., *B. lambicus* and *B. anomalus*). Examples of useful bacteria include, but are not limited to, *Escherichia, Enterobacter, Azotobacter, Erwinia, Klebsielia, Bacillus, Pseudomonas, Proteus*, and *Salmonella.*

Once expressed in a host cell, the PST polypeptides can be used to produce polysialylated products. For example, the PST polypeptides can be isolated using standard protein purification techniques and used in in vitro reactions described herein to make polysialylated products. Partially purified PST polypeptides can also be used in in vitro reactions to make polysialylated products as can the permeabilized host cells. The host cells can also be used in an in vivo system (e.g., fermentative production) to produce polysialylated products.

Typically, the polynucleotide that encodes the PST polypeptides is placed under the control of a promoter that is functional in the desired host cell. An extremely wide variety of promoters are well known, and can be used in the expression vectors of the invention, depending on the particular application. Ordinarily, the promoter selected depends upon the cell in which the promoter is to be active. Other expression control sequences such as ribosome binding sites, transcription termination sites and the like are also optionally included. Constructs that include one or more of these control sequences are termed "expression cassettes." Accordingly, the invention provides expression cassettes into which the nucleic acids that encode fusion proteins are incorporated for high level expression in a desired host cell.

Expression control sequences that are suitable for use in a particular host cell are often obtained by cloning a gene that is expressed in that cell. Commonly used prokaryotic control sequences, which are defined herein to include promoters for transcription initiation, optionally with an operator, along with ribosome binding site sequences, include such commonly used promoters as the beta-lactamase (penicillinase) and lactose (lac) promoter systems (Change et al., *Nature* (1977) 198: 1056), the tryptophan (trp) promoter system (Goeddel et al., *Nucleic Acids Res.* (1980) 8: 4057), the tac promoter (DeBoer, et al., *Proc. Natl. Acad. Sci. U.S.A.* (1983) 80:21-25); and the lambda-derived $P_L$ promoter and N-gene ribosome binding site (Shimatake et al., *Nature* (1981) 292: 128). The particular promoter system is not critical to the invention, any available promoter that functions in prokaryotes can be used.

For expression of PST proteins in prokaryotic cells other than *E. coli*, a promoter that functions in the particular prokaryotic species is required. Such promoters can be obtained from genes that have been cloned from the species, or heterologous promoters can be used. For example, the hybrid trp-lac promoter functions in *Bacillus* in addition to *E. coli.*

A ribosome binding site (RBS) is conveniently included in the expression cassettes of the invention. An RBS in *E. coli*, for example, consists of a nucleotide sequence 3-9 nucleotides in length located 3-11 nucleotides upstream of the initiation codon (Shine and Dalgarno, *Nature* (1975) 254: 34;

Steitz, *In Biological regulation and development: Gene expression* (ed. R. F. Goldberger), vol. 1, p. 349, 1979, Plenum Publishing, NY).

For expression of the PST proteins in yeast, convenient promoters include GAL1-10 (Johnson and Davies (1984) *Mol. Cell. Biol.* 4:1440-1448) ADH2 (Russell et al. (1983) *J. Biol. Chem.* 258:2674-2682), PHO5 (*EMBO J.* (1982) 6:675-680), and MFα (Herskowitz and Oshima (1982) in *The Molecular Biology of the Yeast Saccharomyces* (eds. Strathern, Jones, and Broach) Cold Spring Harbor Lab., Cold Spring Harbor, N.Y., pp. 181-209). Another suitable promoter for use in yeast is the ADH2/GAPDH hybrid promoter as described in Cousens et al., *Gene* 61:265-275 (1987). For filamentous fungi such as, for example, strains of the fungi *Aspergillus* (McKnight et al., U.S. Pat. No. 4,935,349), examples of useful promoters include those derived from *Aspergillus nidulans* glycolytic genes, such as the ADH3 promoter (McKnight et al., EMBO J. 4: 2093 2099 (1985)) and the tpiA promoter. An example of a suitable terminator is the ADH3 terminator (McKnight et al.).

Either constitutive or regulated promoters can be used in the present invention. Regulated promoters can be advantageous because the host cells can be grown to high densities before expression of the fusion proteins is induced. High level expression of heterologous proteins slows cell growth in some situations. An inducible promoter is a promoter that directs expression of a gene where the level of expression is alterable by environmental or developmental factors such as, for example, temperature, pH, anaerobic or aerobic conditions, light, transcription factors and chemicals. Such promoters are referred to herein as "inducible" promoters, which allow one to control the timing of expression of the glycosyltransferase or enzyme involved in nucleotide sugar synthesis. For *E. coli* and other bacterial host cells, inducible promoters are known to those of skill in the art. These include, for example, the lac promoter, the bacteriophage lambda $P_L$ promoter, the hybrid trp-lac promoter (Amann et al. (1983) *Gene* 25: 167; de Boer et al. (1983) *Proc. Nat'l. Acad. Sci. USA* 80: 21), and the bacteriophage T7 promoter (Studier et al. (1986) *J. Mol. Biol.*; Tabor et al. (1985) *Proc. Nat'l. Acad. Sci. USA* 82: 1074-8). These promoters and their use are discussed in Sambrook et al., supra. A particularly preferred inducible promoter for expression in prokaryotes is a dual promoter that includes a tac promoter component linked to a promoter component obtained from a gene or genes that encode enzymes involved in galactose metabolism (e.g., a promoter from a UDPgalactose 4-epimerase gene (galE)). The dual tac-gal promote is described in PCT Patent Application Publ. No. WO98/20111.

A construct that includes a polynucleotide of interest operably linked to gene expression control signals that, when placed in an appropriate host cell, drive expression of the polynucleotide is termed an "expression cassette." Expression cassettes that encode the fusion proteins of the invention are often placed in expression vectors for introduction into the host cell. The vectors typically include, in addition to an expression cassette, a nucleic acid sequence that enables the vector to replicate independently in one or more selected host cells. Generally, this sequence is one that enables the vector to replicate independently of the host chromosomal DNA, and includes origins of replication or autonomously replicating sequences. Such sequences are well known for a variety of bacteria. For instance, the origin of replication from the plasmid pBR322 is suitable for most Gram-negative bacteria. Alternatively, the vector can replicate by becoming integrated into the host cell genomic complement and being replicated as the cell undergoes DNA replication. A preferred expression vector for expression of the enzymes is in bacterial cells is pTGK, which includes a dual tac-gal promoter and is described in PCT Patent Application Publ. NO. WO98/20111.

The construction of polynucleotide constructs generally requires the use of vectors able to replicate in bacteria. A plethora of kits are commercially available for the purification of plasmids from bacteria (see, for example, EasyPrepJ, FlexiPrepJ, both from Pharmacia Biotech; StrataCleanJ, from Stratagene; and, QIAexpress Expression System, Qiagen). The isolated and purified plasmids can then be further manipulated to produce other plasmids, and used to transfect cells. Cloning in *Streptomyces* or *Bacillus* is also possible.

Selectable markers are often incorporated into the expression vectors used to express the polynucleotides of the invention. These genes can encode a gene product, such as a protein, necessary for the survival or growth of transformed host cells grown in a selective culture medium. Host cells not transformed with the vector containing the selection gene will not survive in the culture medium. Typical selection genes encode proteins that confer resistance to antibiotics or other toxins, such as ampicillin, neomycin, kanamycin, chloramphenicol, or tetracycline. Alternatively, selectable markers may encode proteins that complement auxotrophic deficiencies or supply critical nutrients not available from complex media, e.g., the gene encoding D-alanine racemase for Bacilli. Often, the vector will have one selectable marker that is functional in, e.g., *E. coli*, or other cells in which the vector is replicated prior to being introduced into the host cell. A number of selectable markers are known to those of skill in the art and are described for instance in Sambrook et al., supra.

Construction of suitable vectors containing one or more of the above listed components employs standard ligation techniques as described in the references cited above. Isolated plasmids or DNA fragments are cleaved, tailored, and re-ligated in the form desired to generate the plasmids required. To confirm correct sequences in plasmids constructed, the plasmids can be analyzed by standard techniques such as by restriction endonuclease digestion, and/or sequencing according to known methods. Molecular cloning techniques to achieve these ends are known in the art. A wide variety of cloning and in vitro amplification methods suitable for the construction of recombinant nucleic acids are well-known to persons of skill. Examples of these techniques and instructions sufficient to direct persons of skill through many cloning exercises are found in Berger and Kimmel, *Guide to Molecular Cloning Techniques, Methods in Enzymology*, Volume 152, Academic Press, Inc., San Diego, Calif. (Berger); and Current Protocols in Molecular Biology, F. M. Ausubel et al., eds., *Current Protocols*, a joint venture between Greene Publishing Associates, Inc. and John Wiley & Sons, Inc., (1998 Supplement) (Ausubel).

A variety of common vectors suitable for use as starting materials for constructing the expression vectors of the invention are well known in the art. For cloning in bacteria, common vectors include pBR322 derived vectors such as pBLUESCRIPT™, and λ-phage derived vectors. In yeast, vectors include Yeast Integrating plasmids (e.g., YIp5) and Yeast Replicating plasmids (the YRp series plasmids) and pGPD-2. Expression in mammalian cells can be achieved using a variety of commonly available plasmids, including pSV2, pBC12BI, and p91023, as well as lytic virus vectors (e.g., vaccinia virus, adeno virus, and baculovirus), episomal virus vectors (e.g., bovine papillomavirus), and retroviral vectors (e.g., murine retroviruses).

The methods for introducing the expression vectors into a chosen host cell are not particularly critical, and such methods are known to those of skill in the art. For example, the expression vectors can be introduced into prokaryotic cells, including *E. coli*, by calcium chloride transformation, and into eukaryotic cells by calcium phosphate treatment or electroporation. Other transformation methods are also suitable.

Translational coupling may be used to enhance expression. The strategy uses a short upstream open reading frame derived from a highly expressed gene native to the translational system, which is placed downstream of the promoter, and a ribosome binding site followed after a few amino acid codons by a termination codon. Just prior to the termination codon is a second ribosome binding site, and following the termination codon is a start codon for the initiation of translation. The system dissolves secondary structure in the RNA, allowing for the efficient initiation of translation. See Squires, et. al. (1988), *J. Biol. Chem.* 263: 16297-16302.

The PST polypeptides can be expressed intracellularly, or can be secreted from the cell. Intracellular expression often results in high yields. If necessary, the amount of soluble, active fusion protein may be increased by performing refolding procedures (see, e.g., Sambrook et al., supra.; Marston et al., *Bio/Technology* (1984) 2: 800; Schoner et al., *Bio/Technology* (1985) 3: 151). In embodiments in which the PST polypeptides are secreted from the cell, either into the periplasm or into the extracellular medium, the DNA sequence is linked to a cleavable signal peptide sequence. The signal sequence directs translocation of the fusion protein through the cell membrane. An example of a suitable vector for use in *E. coli* that contains a promoter-signal sequence unit is pTA1529, which has the *E. coli* phoA promoter and signal sequence (see, e.g., Sambrook et al., supra.; Oka et al., *Proc. Natl. Acad. Sci. USA* (1985) 82: 7212; Talmadge et al., *Proc. Natl. Acad. Sci. USA* (1980) 77: 3988; Takahara et al., *J. Biol. Chem.* (1985) 260: 2670). In another embodiment, the PST proteins are fused to a subsequence of protein A or bovine serum albumin (BSA), for example, to facilitate purification, secretion, or stability.

The PST polypeptides of the invention can also be further linked to other bacterial proteins. This approach often results in high yields, because normal prokaryotic control sequences direct transcription and translation. In *E. coli*, lacZ fusions are often used to express heterologous proteins. Suitable vectors are readily available, such as the pUR, pEX, and pMR100 series (see, e.g., Sambrook et al., supra.). For certain applications, it may be desirable to cleave the non-poly-sialyltransferase and/or accessory enzyme amino acids from the fusion protein after purification. This can be accomplished by any of several methods known in the art, including cleavage by cyanogen bromide, a protease, or by Factor $X_a$ (see, e.g., Sambrook et al., supra.; Itakura et al., *Science* (1977) 198: 1056; Goeddel et al., *Proc. Natl. Acad. Sci. USA* (1979) 76: 106; Nagai et al., *Nature* (1984) 309: 810; Sung et al., *Proc. Natl. Acad. Sci. USA* (1986) 83: 561). Cleavage sites can be engineered into the gene for the fusion protein at the desired point of cleavage.

More than one recombinant protein may be expressed in a single host cell by placing multiple transcriptional cassettes in a single expression vector, or by utilizing different selectable markers for each of the expression vectors which are employed in the cloning strategy. For instance, a sialyltransferase, e.g., a CST-II protein, and a PST polypeptide can be expressed in the same host expression system. The lysates of such host cells or purified sialyltransferase and PST polypeptides can then be used to transfer sialic acid residues.

VI. Purification of PST Polypeptides

The PST proteins of the present invention can be expressed, e.g., as intracellular proteins or as proteins that are secreted from the cell, and can be used in this form, in the methods of the present invention. For example, a crude cellular extract containing the expressed intracellular or secreted PST polypeptide can used in the methods of the present invention.

Alternatively, the PST polypeptide can be purified according to standard procedures of the art, including ammonium sulfate precipitation, affinity columns, column chromatography, gel electrophoresis and the like (see, generally, R. Scopes, *Protein Purification*, Springer-Verlag, N.Y. (1982), Deutscher, *Methods in Enzymology Vol. 182: Guide to Protein Purification*., Academic Press, Inc. N.Y. (1990)). Substantially pure compositions of at least about 70, 75, 80, 85, 90% homogeneity are preferred, and 92, 95, 98 to 99% or more homogeneity are most preferred. The purified proteins may also be used, e.g., as immunogens for antibody production.

To facilitate purification of the PST polypeptides of the invention, the nucleic acids that encode the proteins can also include a coding sequence for an epitope or "tag" for which an affinity binding reagent is available, i.e. a purification tag. Examples of suitable epitopes include the myc and V-5 reporter genes; expression vectors useful for recombinant production of fusion proteins having these epitopes are commercially available (e.g., Invitrogen (Carlsbad Calif.) vectors pcDNA3.1/Myc-His and pcDNA3.1/V5-His are suitable for expression in mammalian cells). Additional expression vectors suitable for attaching a tag to a PST polypeptide of the invention, and corresponding detection systems are known to those of skill in the art, and several are commercially available (e.g., FLAG" (Kodak, Rochester N.Y.). Another example of a suitable tag is a polyhistidine sequence, which is capable of binding to metal chelate affinity ligands. Typically, six adjacent histidines are used, although one can use more or less than six. Suitable metal chelate affinity ligands that can serve as the binding moiety for a polyhistidine tag include nitrilo-tri-acetic acid (NTA) (Hochuli, E. (1990) "Purification of recombinant proteins with metal chelating adsorbents" In Genetic Engineering Principles and Methods, J. K. Setlow, Ed., Plenum Press, NY; commercially available from Qiagen (Santa Clarita, Calif.)). Other purification or epitope tags include, e.g., AU1, AU5, DDDDK (EC5), E tag, E2 tag, Glu-Glu, a 6 residue peptide, EYMPME, derived from the Polyoma middle T protein, HA, HSV, IRS, KT3, S tage, S1 tag, T7 tag, V5 tag, VSV-G, β-galactosidase, Gal4, green fluorescent protein (GFP), luciferase, protein C, protein A, cellulose binding protein, GST (glutathione S-transferase), a step-tag, Nus-S, PPI-ases, Pfg 27, calmodulin binding protein, dsb A and fragments thereof, and granzyme B. Epitope peptides and antibodies that bind specifically to epitope sequences are commercially available from, e.g., Covance Research Products, Inc.; Bethyl Laboratories, Inc.; Abcam Ltd.; and Novus Biologicals, Inc.

Purification tags also include maltose binding domains and starch binding domains. Proteins comprising purification tags can be purified using a binding partner that binds the purification tag, e.g., antibodies to the purification tag, nickel or cobalt ions or resins, and amylose, maltose, or a cyclodextrin. Purification tags also include starch binding domains, *E. coli* thioredoxin domains (vectors and antibodies commercially available from e.g., Santa Cruz Biotechnology, Inc. and Alpha Diagnostic International, Inc.), and the carboxy-terminal half of the SUMO protein (vectors and antibodies commercially available from e.g., Life Sensors Inc.). Starch binding domains, such as a maltose binding domain from *E. coli* and SBD (starch binding domain) from an amylase of *A. niger*, are described in WO 99/15636, herein incorporated by reference. Affinity purification of a fusion protein comprising a starch binding domain using a betacyclodextrin (BCD)-derivatized resin is described in WO 2005/014779, published Feb. 17, 2005, herein incorporated by reference in its entirety. In some embodiments, a PST polypeptide comprises more than one purification or epitope tag.

Other haptens that are suitable for use as tags are known to those of skill in the art and are described, for example, in the Handbook of Fluorescent Probes and Research Chemicals (6th Ed., Molecular Probes, Inc., Eugene Oreg.). For example, dinitrophenol (DNP), digoxigenin, barbiturates (see, e.g., U.S. Pat. No. 5,414,085), and several types of fluorophores are useful as haptens, as are derivatives of these compounds. Kits are commercially available for linking haptens and other moieties to proteins and other molecules. For example, where the hapten includes a thiol, a heterobifunctional linker such as SMCC can be used to attach the tag to lysine residues present on the capture reagent.

One of skill would recognize that modifications can be made to the catalytic or functional domains of the PST polypeptide without diminishing their biological activity. Some modifications may be made to facilitate the cloning, expression, or incorporation of the catalytic domain into a fusion protein. Such modifications are well known to those of skill in the art and include, for example, the addition of codons at either terminus of the polynucleotide that encodes the catalytic domain to provide, for example, a methionine added at the amino terminus to provide an initiation site, or additional amino acids (e.g., poly His) placed on either terminus to create conveniently located restriction enzyme sites or termination codons or purification sequences.

VII. Donor Substrates and Acceptor Substrates

Suitable donor substrates used by the PST polypeptides and other glycosyltransferases in the methods of the invention include, but are not limited to, UDP-Glc, UDP-GlcNAc, UDP-Gal, UDP-GalNAc, GDP-Man, GDP-Fuc, UDP-GlcUA, and CMP-sialic acid and other activated sialic acid moieties. Guo et al., *Applied Biochem. and Biotech.* 68: 1-20 (1997).

Typically, an acceptor substrate for a PST enzyme includes a terminal sialic acid in an α-2,3 linkage for addition of a second sialic acid in an α-2,8 linkage, or a terminal sialic acid in an α-2,8 linkage for addition of one or more sialic acid moieties in an α-2,8 linkage.

Acceptor substrates for addition of a the first sialic acid include e.g., a terminal galactose for addition of a sialic acid moiety in an α-2,3 linkage. Typically, an acceptor substrate for a PST enzyme includes a terminal sialic acid in an α-2,3 linkage for addition of a second sialic acid in an α-2,8 linkage, or a terminal sialic acid in an α-2,8 linkage for addition of one or more sialic acid moieties in an α-2,8 linkage. Examples of suitable acceptors include a terminal Gal that is linked to GlcNAc or Glc by a β1,4 linkage, and a terminal Gal that is β1,3-linked to either GlcNAc or GalNAc. Suitable acceptors, include, for example, galactosyl acceptors such as Galβ1,4GlcNAc, Galβ1,4GalNAc, Galβ1,3GalNAc, lacto-N-tetraose, Galβ1,3GlcNAc, Galβ1,3Ara, Galβ1,6GlcNAc, Galβ1,4Glc (lactose), and other acceptors known to those of skill in the art. The terminal residue to which the galactose moiety is attached can itself be attached to, for example, H, a saccharide, oligosaccharide, or an aglycone group having at least one carbohydrate atom. In some embodiments, the acceptor residue is a portion of an oligosaccharide that is attached to a peptide, a protein, a lipid, or a proteoglycan, for example.

Suitable acceptor substrates used by the poly-sialyltransferase polypeptides and methods of the invention include, but are not limited to, polysaccharides and oligosaccharides. The poly-sialyltransferase polypeptides described herein can also be used in multienzyme systems to produce a desired product from a convenient starting material.

Suitable acceptor substrates used by the PST polypeptides and methods of the invention include, but are not limited to, proteins, lipids, gangliosides and other biological structures (e.g., whole cells) that can be modified by the methods of the invention. These acceptor substrates will typically comprise the polysaccharide or oligosaccharide molecules described above.

The present invention provides PST polypeptides that are selected for their ability to produce oligosaccharides, glycoproteins and glycolipids having desired oligosaccharide moieties. Similarly, if present, accessory enzymes are chosen based on an desired activated sugar substrate or on a sugar found on the product oligosaccharide, for example, a sialyltransferase capable of priming the reaction by adding an appropriate sialic acid residue to the substrate.

For synthesis of glycoproteins, one can readily identify suitable poly-sialyltransferase polypeptides by reacting various amounts of a poly-sialyltransferase polypeptide of interest (e.g., 0.01-100 mU/mg protein) with a glycoprotein (e.g., at 1-10 mg/ml) to which is linked an oligosaccharide that has a potential acceptor site for glycosylation by the poly-sialyltransferase protein of interest. The abilities of the recombinant poly-sialyltransferase proteins of the present invention to add a sugar residue at the desired acceptor site are compared to a known poly-sialyltransferase polypeptide having the desired property (e.g., acceptor substrate specificity or catalytic activity).

In general, the efficacy of the enzymatic synthesis of poly-sialylated oligosaccharides, glycoproteins, and glycolipids can be enhanced through use of recombinantly produced truncated poly-sialyltransferase polypeptides of the present invention. Recombinant techniques enable production of the truncated, more soluble poly-sialyltransferase polypeptides in the large amounts that are required for large-scale in vitro oligosaccharide, glycoprotein and glycolipid modification.

In some embodiments, suitable oligosaccharides, glycoproteins, and glycolipids for use by the poly-sialyltransferase polypeptides and methods of the invention can be glycoproteins and glycolipids immobilized on a solid support during the glycosylation reaction. The term "solid support" also encompasses semi-solid supports. In some embodiments, the target glycoprotein or glycolipid is reversibly immobilized so that the respective glycoprotein or glycolipid can be released after the glycosylation reaction is completed. Many suitable matrices are known to those of skill in the art. Ion exchange, for example, can be employed to temporarily immobilize a glycoprotein or glycolipid on an appropriate resin while the glycosylation reaction proceeds. A ligand that specifically binds to the glycoprotein or glycolipid of interest can also be used for affinity-based immobilization. For example, antibodies that specifically bind to a glycoprotein are suitable. Also, where the glycoprotein of interest is itself an antibody or contains a fragment thereof, one can use protein A or G as the affinity resin. Dyes and other molecules that specifically bind to a glycoprotein or glycolipid of interest are also suitable.

When the acceptor saccharide is a truncated version of the full-length glycoprotein, in some embodiments, it includes the biologically active subsequence of the full-length glycoprotein. Exemplary biologically active subsequences include, but are not limited to, enzyme active sites, receptor binding sites, ligand binding sites, complementarity determining regions of antibodies, and antigenic regions of antigens.

VIII. Production of Polysialylated Products

PST polypeptides can be used to make poly-sialylated products in in vitro reactions mixes or by in vivo reactions, e.g., by fermentative growth of recombinant microorganisms that comprise nucleotides that encode PST polypeptides.

A. In Vitro Reactions

The PST polypeptides can be used to make poly-sialylated products in in vitro reactions mixes. The in vitro reaction mixtures can include permeabilized microorganisms comprising the PST polypeptides, partially purified PST polypeptides, or purified PST polypeptides; as well as donor substrates acceptor substrates, and appropriate reaction buffers. For in vitro reactions, the recombinant glycosyltransferase proteins, such as PST polypeptides, acceptor substrates, donor substrates and other reaction mixture ingredients are combined by admixture in an aqueous reaction medium. Additional glycosyltransferases can be used in combination with the PST polypeptides, depending on the desired PST product. The medium generally has a pH value of about 5 to about 8.5. The selection of a medium is based on the ability of the medium to maintain pH value at the desired level. Thus, in some embodiments, the medium is buffered to a pH value of about 7.5. If a buffer is not used, the pH of the medium should be maintained at about 5 to 8.5, depending upon the particular glycosyltransferase used. For PST polypeptides, the pH range is maintained from about 5.5 to 8.0.

Enzyme amounts or concentrations are expressed in activity units, which is a measure of the initial rate of catalysis. One activity unit catalyzes the formation of 1 μmol of product per minute at a given temperature (typically 37° C.) and pH value (typically 7.5). Thus, 10 units of an enzyme is a catalytic amount of that enzyme where 10 μmol of substrate are converted to 10 μmol of product in one minute at a temperature of 37° C. and a pH value of 7.5.

The reaction mixture may include divalent metal cations ($Mg^{2+}$, $Mn^{2+}$). The reaction medium may also comprise solubilizing detergents (e.g., Triton or SDS) and organic solvents such as methanol or ethanol, if necessary. The enzymes can be utilized free in solution or can be bound to a support such as a polymer. The reaction mixture is thus substantially homogeneous at the beginning, although some precipitate can form during the reaction.

The temperature at which an above process is carried out can range from just above freezing to the temperature at which the most sensitive enzyme denatures. That temperature range is preferably about 0° C. to about 45° C., and more preferably at about 20° C. to about 37° C.

The reaction mixture so formed is maintained for a period of time sufficient to obtain the desired high yield of polysialylated product. For large-scale preparations, the reaction will often be allowed to proceed for between about 0.5-240 hours, and more typically between about 1-36 hours.

B. In Vivo Reactions

The PST polypeptides can be used to make poly-sialylated products by in in vivo reactions, e.g., fermentative growth of recombinant microorganisms comprising the PST polypeptides. Fermentative growth of recombinant microorganisms can occur in the presence of medium that includes an acceptor substrate and a donor substrate or a precursor to a donor substrate, e.g., galactose or GalNAc. See, e.g., Priem et al., *Glycobiology* 12:235-240 (2002). The microorganism takes up the acceptor substrate and the donor substrate and the precursor to a donor substrate and the addition of the donor substrate to the acceptor substrate takes place in the living cell. The microorganism can be altered to facilitate uptake of the acceptor substrate, e.g., by expressing a sugar transport protein. For example, where lactose is the acceptor saccharide, *E. coli* cells that express the LacY permease can be used. Other methods can be used to decrease breakdown of an acceptor saccharide or to increase production of a donor saccharide or a precursor of the donor saccharide. In some embodiments, production of poly-sialylated products is enhanced by manipulation of the host microorganism. For example, in *E. coli*, break down of sialic acid can be minimized by using a host strain that is lack CMP-sialate synthase (NanA–). (In *E. coli*, CMP-sialate synthase appears to be a catabolic enzyme.) Also in *E. coli*, when lactose is, for example, the acceptor saccharide or an intermediate in synthesizing the poly-sialylated product, lactose breakdown can be minimized by using host cells that are LacZ–. Methods for in vivo synthesis of oligosaccharides, including oligosaccharides containing sialic acid are found in, e.g., Samain and Priem WO/2001/004341 (2001) and Johnson et al. WO/2006/034225 (2006).

In some embodiments, the in vivo polysialylation system can also comprise a sialyltransferase to provide a primed substrate for the PST of the present invention.

C. Characterization of and Isolation of Poly-Sialylated Products

The production of poly-sialylated products can be monitored by e.g., determining that production of the desired product has occurred or by determining that a substrate such as the acceptor substrate has been depleted. Those of skill will recognize that poly-sialylated products such as oligosaccharide, can be identified using techniques such as chromatography, e.g., using paper or TLC plates, or by mass spectrometry, e.g., MALDI-TOF spectrometry, or by NMR spectroscopy. Methods of identification of poly-sialylated products are known to those of skill in the art and are found, e.g., in U.S. Pat. No. 6,699,705, which is herein incorporated by reference for all purposes and in Varki et al., *Preparation and Analysis of Glycoconjugates*, in Current Protocols in Molecular Biology, Chapter 17 (Ausubel et al. eds, 1993).

In some embodiments, the PST polypeptides and methods of the present invention are used to enzymatically synthesize a glycoprotein or glycolipid that has a substantially uniform glycosylation pattern. The glycoproteins and glycolipids include a saccharide or oligosaccharide that is attached to a protein, glycoprotein, lipid, or glycolipid for which a glycoform alteration is desired. The saccharide or oligosaccharide includes a structure that can function as an acceptor substrate for a glycosyltransferase. When the acceptor substrate is glycosylated, the desired oligosaccharide moiety is formed. The desired oligosaccharide moiety is one that imparts the desired biological activity upon the glycoprotein or glycolipid to which it is attached. In the compositions of the invention, the pre-selected saccharide residue is linked to at least about 30% of the potential acceptor sites of interest. More preferably, the pre-selected saccharide residue is linked to at least about 50% of the potential acceptor substrates of interest, and still more preferably to at least 70% of the potential acceptor substrates of interest. In situations in which the starting glycoprotein or glycolipid exhibits heterogeneity in the oligosaccharide moiety of interest (e.g., some of the oligosaccharides on the starting glycoprotein or glycolipid already have the pre-selected saccharide residue attached to the acceptor substrate of interest), the recited percentages include such pre-attached saccharide residues.

The term "altered" refers to the glycoprotein or glycolipid of interest having a glycosylation pattern that, after application of the PST polypeptides and methods of the invention, is different from that observed on the glycoprotein as originally produced. An example of such glycoconjugates are glycoproteins in which the glycoforms of the glycoproteins are different from those found on the glycoprotein when it is produced by cells of the organism to which the glycoprotein is native. Also provided are poly-sialyltransferase polypeptides and methods of using such proteins for enzymatically synthesizing glycoproteins and glycolipids in which the glycosylation pattern of these glycoconjugates are modified compared to the glycosylation pattern of the glycoconjugates as originally produced by a host cell, which can be of the same or a different species than the cells from which the native glycoconjugates are produced.

One can assess differences in glycosylation patterns not only by structural analysis of the glycoproteins and glycolipids, but also by comparison of one or more biological activities of the glycoconjugates. For example, a glycoprotein having an "altered glycoform" includes one that exhibits an improvement in one more biological activities of the glycoprotein after the glycosylation reaction compared to the unmodified glycoprotein. For example, an altered glycoconjugate includes one that, after application of the poly-sialyltransferase polypeptides and methods of the invention, exhibits a greater binding affinity for a ligand or receptor of interest, a greater therapeutic half-life, reduced antigenicity, and targeting to specific tissues. The amount of improvement observed is preferably statistically significant, and is more preferably at least about a 25% improvement, and still more preferably is at least about 30%, 40%, 50%, 60%, 70%, and even still more preferably is at least 80%, 90%, or 95%.

The products produced using PST polypeptides can be used without purification. However, standard, well known techniques, for example, thin or thick layer chromatography, ion exchange chromatography, or membrane filtration can be used for recovery of glycosylated saccharides. Also, for example, membrane filtration, utilizing a nanofiltration or reverse osmotic membrane as described in commonly assigned AU Patent No. 735695 may be used. As a further example, membrane filtration wherein the membranes have a molecular weight cutoff of about 1000 to about 10,000 Daltons can be used to remove proteins. As another example, nanofiltration or reverse osmosis can then be used to remove salts. Nanofilter membranes are a class of reverse osmosis membranes which pass monovalent salts but retain polyvalent salts and uncharged solutes larger than about 200 to about 1000 Daltons, depending upon the membrane used. Thus, for example, the oligosaccharides produced by the compositions and methods of the present invention can be retained in the membrane and contaminating salts will pass through.

It must be noted that as used herein and in the appended claims, the singular forms "a", "and", and "the" include plural referents unless the context clearly dictates otherwise. Thus, for example, reference to "a nucleic acid" includes a plurality of such nucleic acids and reference to "the polypeptide" includes reference to one or more polypeptides and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. All citations are incorporated herein by reference.

EXAMPLES

Various naturally-occurring polysialyl-transferase (PST) proteins have polysialyltransferase activity. The present study identifies core PST structures required for poly-sialyltransferase activity and surprisingly improved enzymatic activities and solubility associated with modified PST proteins.

Example 1

N-Terminal PST Truncations

The following experiments are based on truncation products of PST-13 (an N-terminal MalE fusion to the full length sialyltransferase from Neisseria meningitidis. Upon analysis of the N-terminal end of the PST protein it was found to consist of a relatively high number of basic and aromatic residues (there are 6 lysines in the first 14 amino acids).

Two truncations were made: a 19 residue truncation (indicated below by the underlined M) and a 32 residue truncation (indicated below by the underlined R):

(SEQ ID NO: 6)
NH$_2$-MLKKIKKALFQPKKFFQDS<u>M</u>WLTTSPFYLTPP<u>R</u>NNLFVISNLGQLN

QVQSLIK . . .

The two truncations are: PST-29 (MalE-Pst$_{\Delta 19}$) and PST-30 (MalE-Pst$_{\Delta 32}$).

Example 2

Solubility Assessment of the PST Truncations

To compare the solubility of the two truncated proteins with that of the full length parent protein, the constructs were transformed into E. coli AD202 and grown in 2YT media with 150 ug/mL ampicillin. The culture was inoculated with overnight culture for an OD$_{600}$ of ~0.1. Cells were grown at 37° C. for about 2 h with shaking at 200 rpm to reach an OD$_{600}$ of 0.2-0.5. Culture was induced with 0.5 uM IPTG and incubated at 20° C. for ~24 hours with shaking at 200 rpm. The final OD$_{600}$ was about 4-5. The cells were harvested, lysed and centrifuged. Both pellet and supernatants of the lysed cells overexpressing the PST constructs were collected for analysis.

Figure 2:
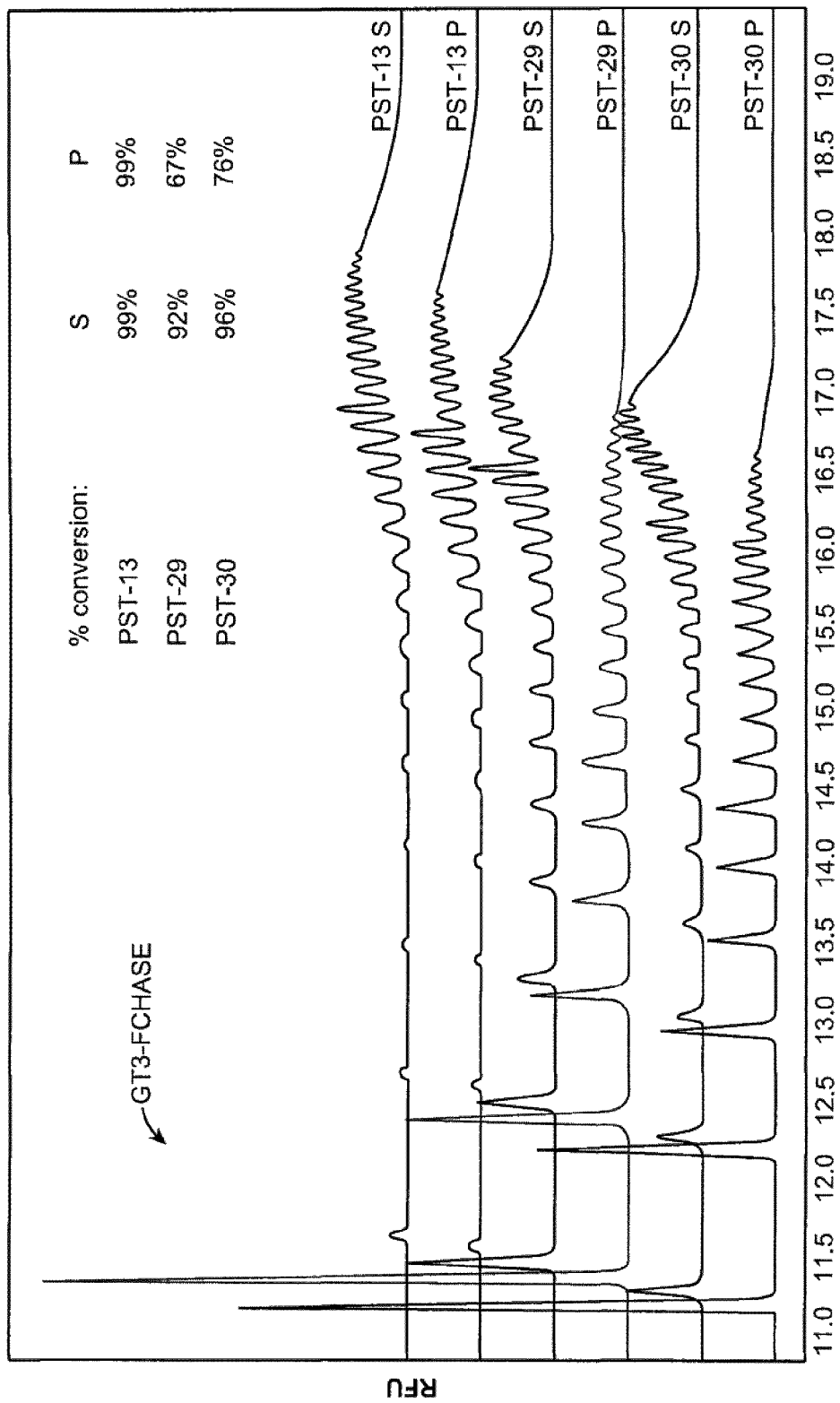
FIG. 2 provides a representative capillary electrophoresis (CE) electropherogram of a PST sialyltransferase reaction. The analysis is of the 27,000×g supernatants (S) and pellets (P) of PST-13 (MalE-full length PST), PST-29 (MalE-PST-Δ19) and PST-30 (MalE-PST-Δ32). Percent conversion indicates the percentage of the substrate converted to any sialylated form.
Figure 3:
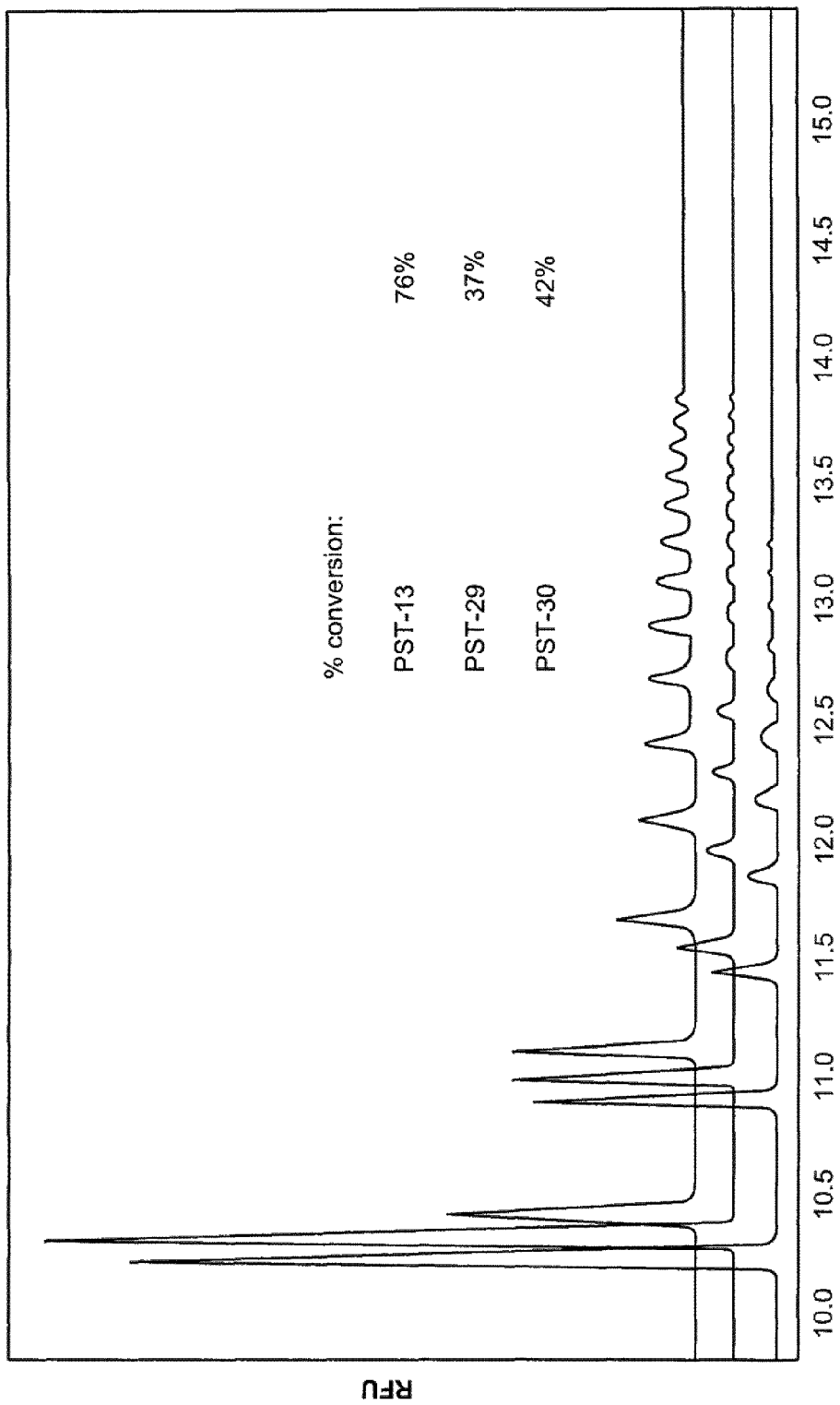
FIG. 3 provides a representative CE analysis of 1/10 diluted 27,000×g supernatants of PST-13 (MalE-full length PST), PST-29 (MalE-PST-Δ19) and PST-30 (MalE-PST-Δ32). Percent conversion indicates the percentage of the substrate converted to any sialylated form. The CE lines are ordered to correspond to PST-13 (MalE-full length PST), PST-29 (MalE-PST-Δ19) and PST-30 (MalE-PST-Δ32) from top to bottom.
Figure 4:
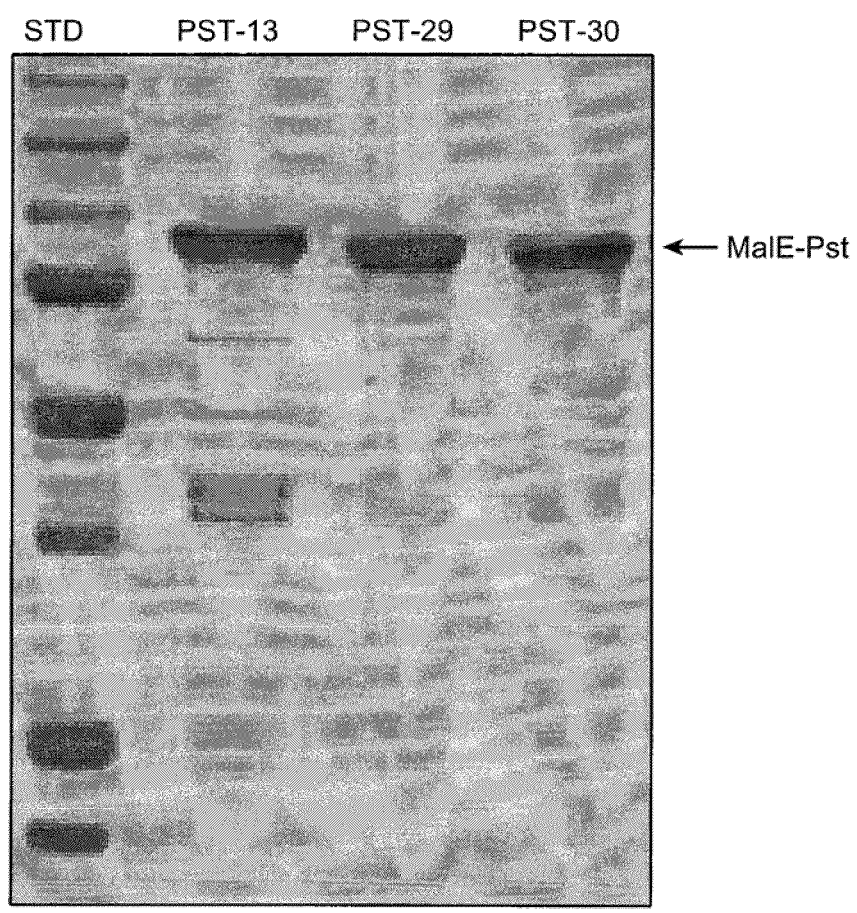
FIG. 4 depicts a representative SDS-PAGE of purified PST-13 (MalE-full length PST), PST-29 (MalE-PST-Δ19) and PST-30 (MalE-PST-Δ32). The arrow indicates the approximate expected migration point for the purified protein bands.

As shown in FIG. 1, SDS-PAGE analysis indicates that both mutants expressed well. The levels of expression of the PST-13 (MalE-full length PST) construct were higher, but in contrast to the PST-13 (MalE-full length PST) construct, the two truncations remained almost entirely in the 27,000×g supernatant indicating they are more soluble. Activity assays were performed on the GT3-FCHASE substrate using the following reaction conditions: 0.5 mM GT3-FCHASE, 50 mM NaHEPES pH 7.5, 10 mM MgCl$_2$, 10 mM CMP-NeuAC, 10% enzyme at 37° C. for 5 minutes. As seen in the CE analysis (shown in FIG. 2) the truncations were active. The assays for the 27,000×g supernatants were repeated with a 1/10 dilution of enzyme for direct comparison (FIG. 3). The results depicted in FIG. 3 indicate that PST-13 (MalE-full length PST) was more active than both truncations.

Example 3

Purification of the Truncated PST Proteins

Figure 15:
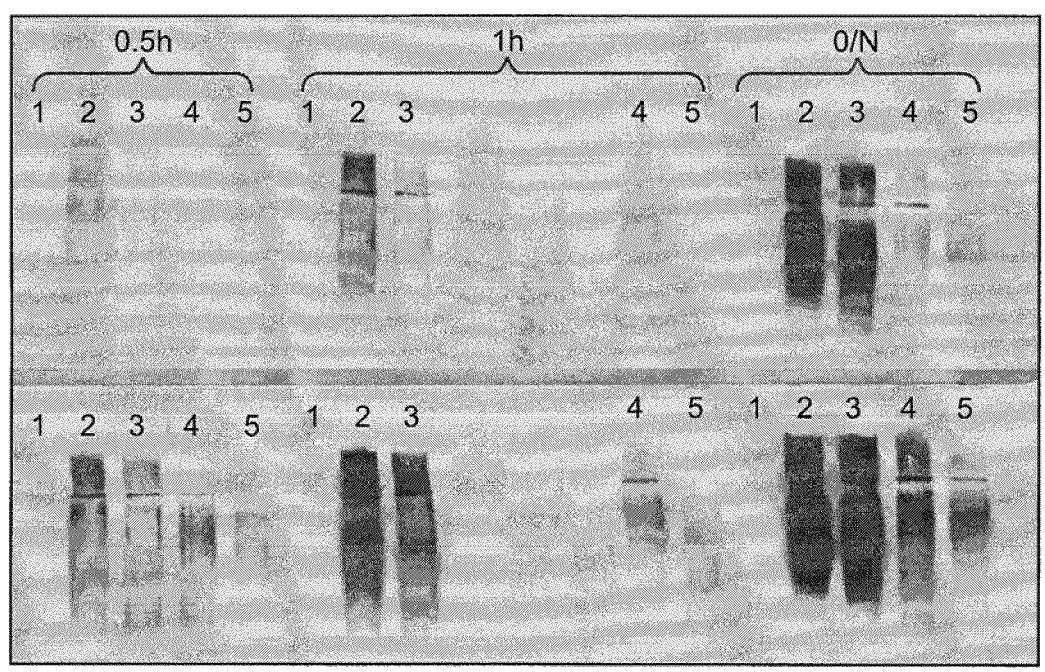
FIG. 15 provides the results of increasing Fetuin substrate concentration on polysialic acid chain length. The figure shows Western blots (two exposure times) of poly-sialylated Fetuin product after incubation with PST-30 (MalE-PST-Δ32) and CMP-sialic acid, for the indicated times, i.e., 0.5 hours, one hour and overnight. The lanes are numbered as follows: Lane 1, no Fetuin control; Lane 2, no CMP-sialic acid control; Lane 3, 1.0 mg/ml Fetuin; Lane 4, 2.5 mg/m. Fetuin; Lane 5, 5.0 mg/ml Fetuin.

In order to determine relative specific activity, all three proteins were first purified by affinity chromatography. Five mL of 27,000×g supernatant was passed through a 8 mL amylose column and eluted with 10 mM maltose. The chromatograms from all three proteins look almost identical. In the past, PST-13 (MalE-full length PST) has been difficult to concentrate by centrifugation as it precipitates on the membrane. To see if the truncations would behave in the same way, 5 mL of each purified protein was centrifuged in Amicon Ultra-4 centrifugation filters (Millipore) for 25 min. The typical white precipitate occurred on the membrane for PST-13 (MalE-full length PST) which was concentrated to 1.5 mL. There was a very small amount of precipitate on the PST-29 (MalE-PST-Δ19) and PST-30 (MalE-PST-Δ32) membranes but not nearly as much as the parent and the truncations were able to concentrate to 0.8 mL in the same time. Protein concentrations of the enzymes were determined by BCA assay (Pierce) and then 3 μg of each was loaded on an SDS-PAGE gel (FIG. 15). PST-29 (MalE-PST-Δ19) appeared to be the most pure though both truncations were purified to a greater degree than the parent.

Figure 5:
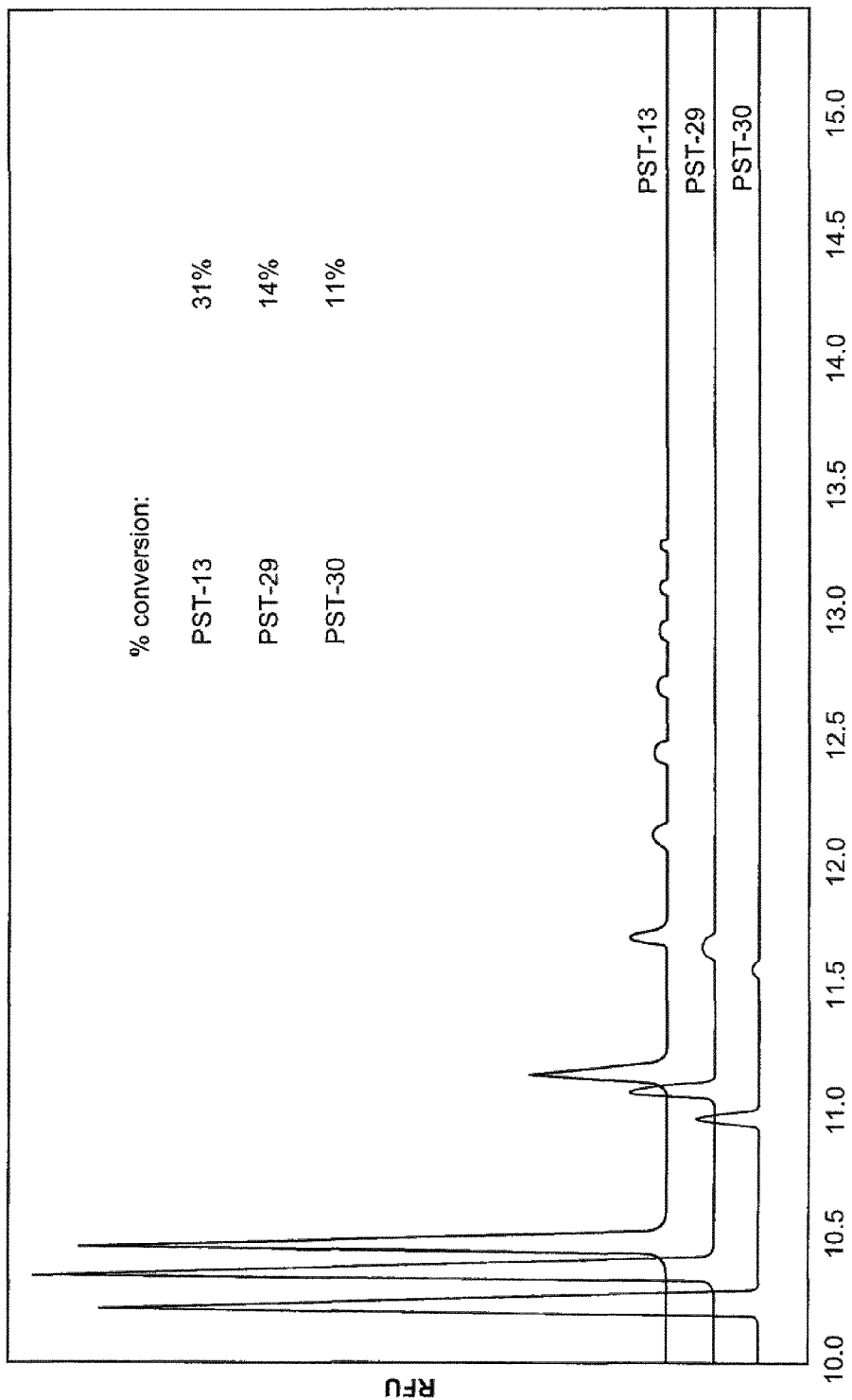
FIG. 5 depicts a representative CE analysis showing the activity of 50 ng of purified MalE-Pst fusion constructs: PST-13 (MalE-full length PST), PST-29 (MalE-PST-Δ19) and PST-30 (MalE-PST-Δ32). Percent conversion indicates the percentage of substrate converted into sialylated product.

To determine the relative specific activity of the purified truncation proteins, 50 ng of each protein was added to a reaction with GT3-FCHASE (reaction conditions described above) by making a 50 ng/μL solution of each PST and then adding 1 μL of enzyme to the reaction. Because of the high concentration of the two truncated enzymes dilution was required for an accurate activity comparison among the enzymes. As shown FIG. 5, under the conditions tested, PST-13 (MalE-full length PST) exhibits an activity roughly three times higher than the activity of the two truncated proteins.

Example 4

Solubility Analysis of the Truncated PSTs

Figure 6:
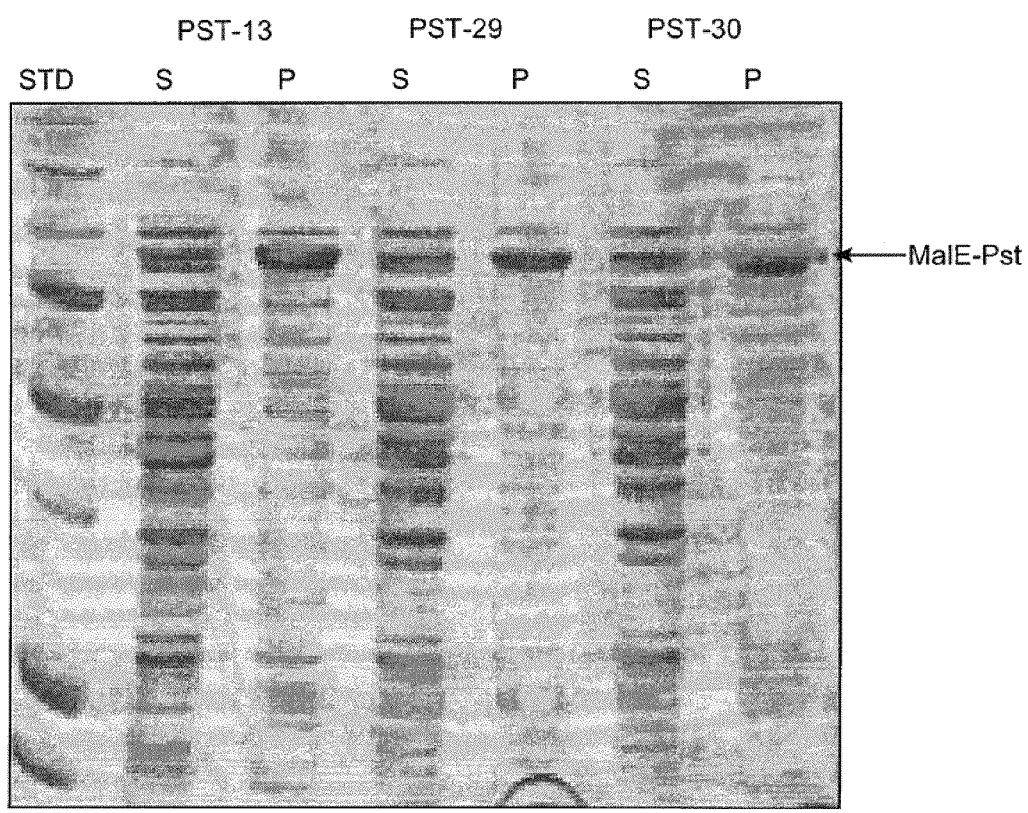
FIG. 6 depicts SDS-PAGE analysis of a 100,000×g centrifugation of PST-13 (MalE-full length PST), PST-29 (MalE-PST-Δ19) and PST-30 (MalE-PST-Δ32). "S" indicates the supernatant (soluble) fraction and "P" indicates the pellet fraction.
Figure 7:
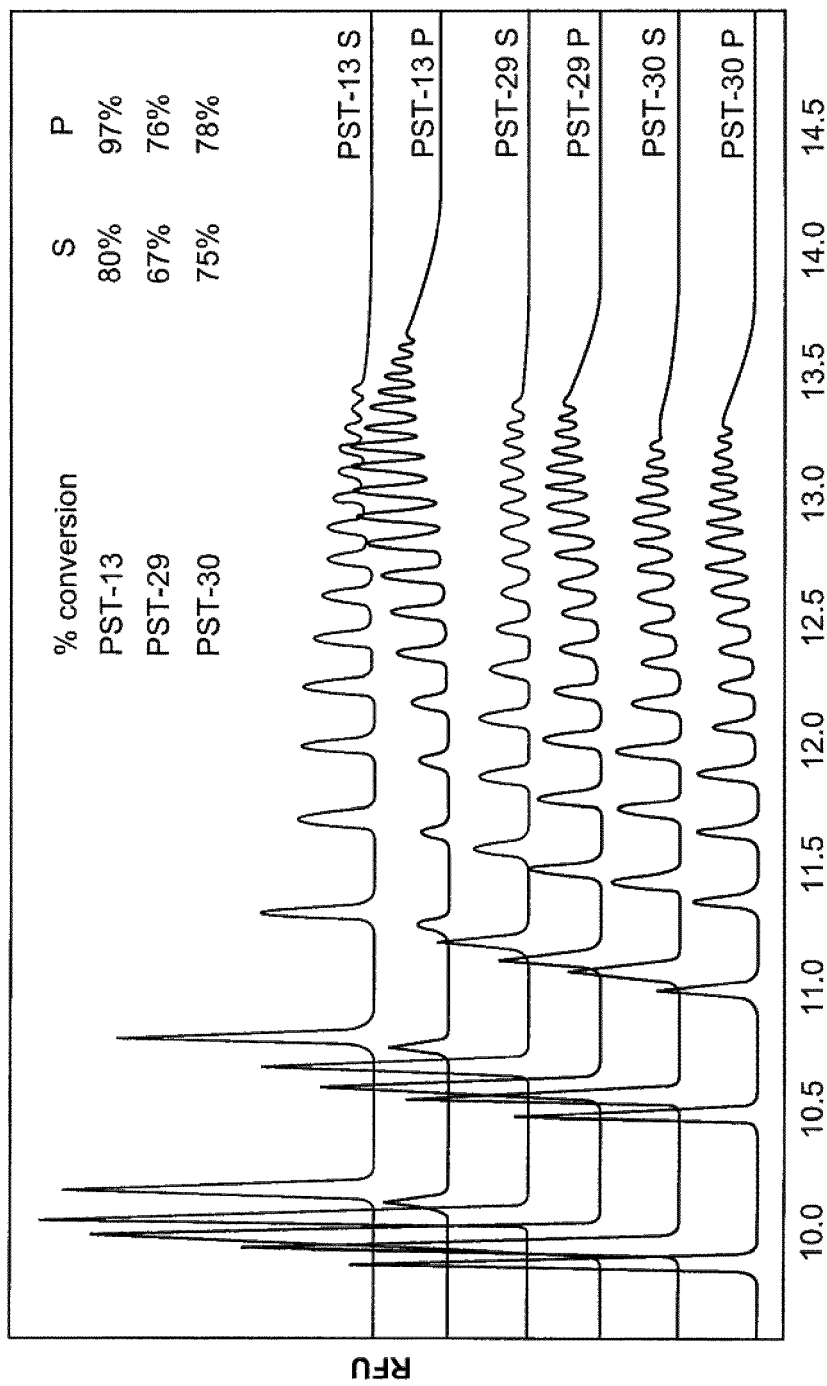
FIG. 7 shows a representative CE analysis of the 100,000×g centrifugation assays for PST-13 (MalE-full length PST), PST-29 (MalE-PST-Δ19) and PST-30 (MalE-PST-Δ32). "S" indicates the supernatant (soluble) fraction and "P" indicates the pellet fraction. Percent conversion indicates the percentage of substrate converted to sialylated product.

To test the solubility of the truncations, 5 mL of each 27,000×g supernatant was centrifuged at 100,000×g for 60 min at 4° C. The pellets were resuspended in 5 mL buffer in order to directly compare with the supernatant. Three μL of each sample was analyzed by SDS-PAGE as shown in FIG. 6. In all three cases, most of the enzyme appeared to have pelleted. However, analysis of activity (FIG. 7) shows that the relative amount of enzyme found in the supernatant versus the pellets is higher for the two truncations and in fact, the activity of PST-30 is fairly equally distributed between the supernatant and pellet. The enzymes' solubility makes them attractive candidates to be used as reagents for modification of more complex substrates, e.g., oligosaccharides, glycoproteins and glycolipids.

Example 5

PST Stability Analysis

Figure 8:
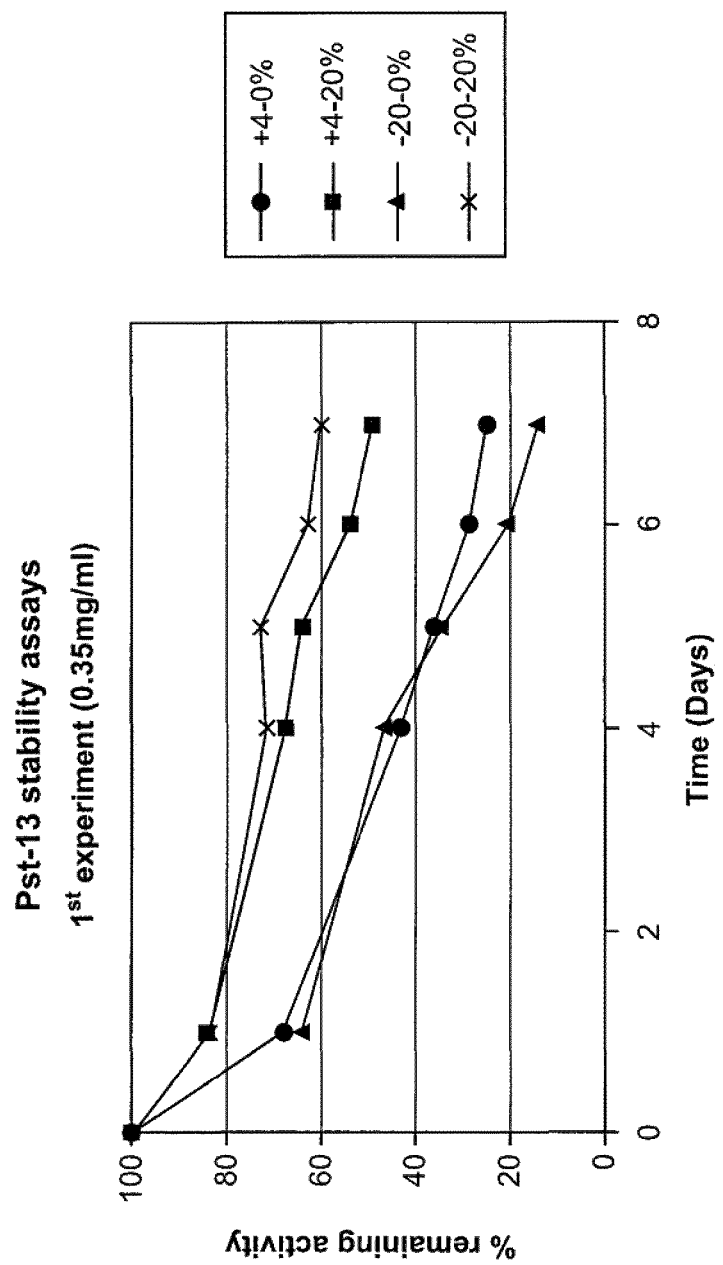
FIG. 8 provides a representative graph depicting the results of PST-13 (MalE-full length PST) stability assays. A concentration of 0.35 mg/ml of PST-13 (MalE-full length PST) was used in the assay. Time (in days) is plotted on the X-axis, while remaining activity (%) is plotted on the Y axis.
Figure 9:
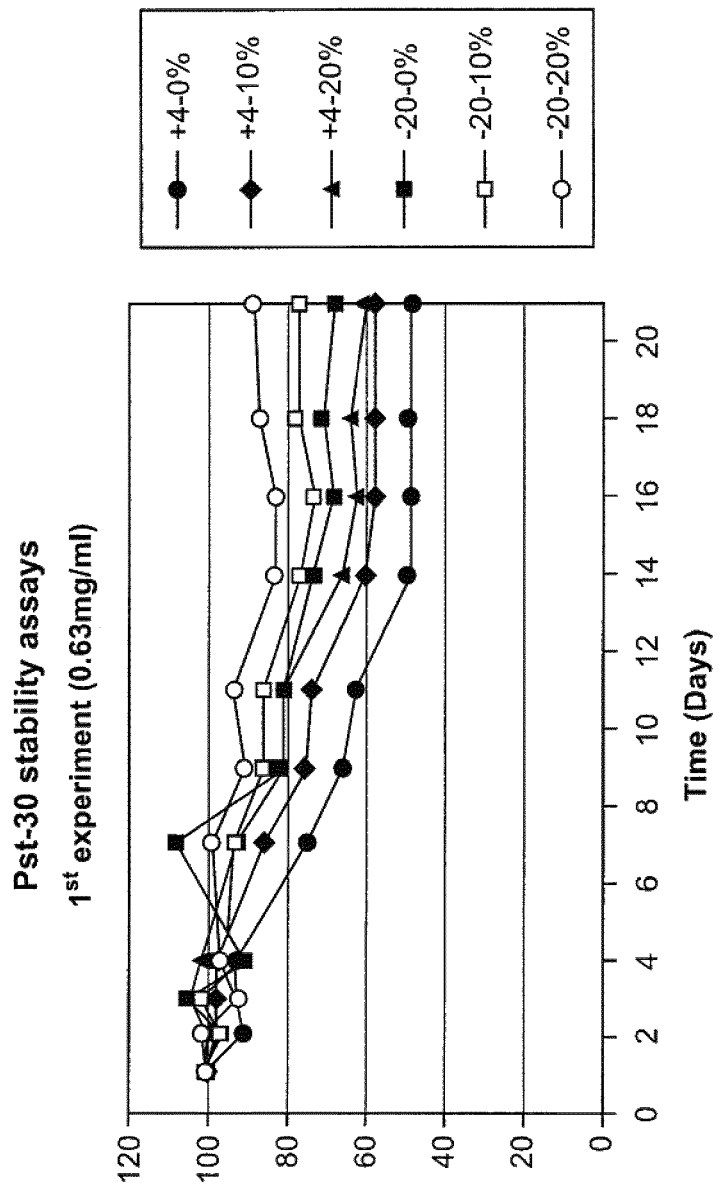
FIG. 9 provides a graph depicting the results PST-30 (MalE-PST-Δ32) stability assays. A concentration of 1.63 mg/ml of PST-30 (MalE-PST-Δ32) was used. Time (in days) is plotted on the X-axis, while remaining activity (%) is plotted on the Y axis.
Figure 10:
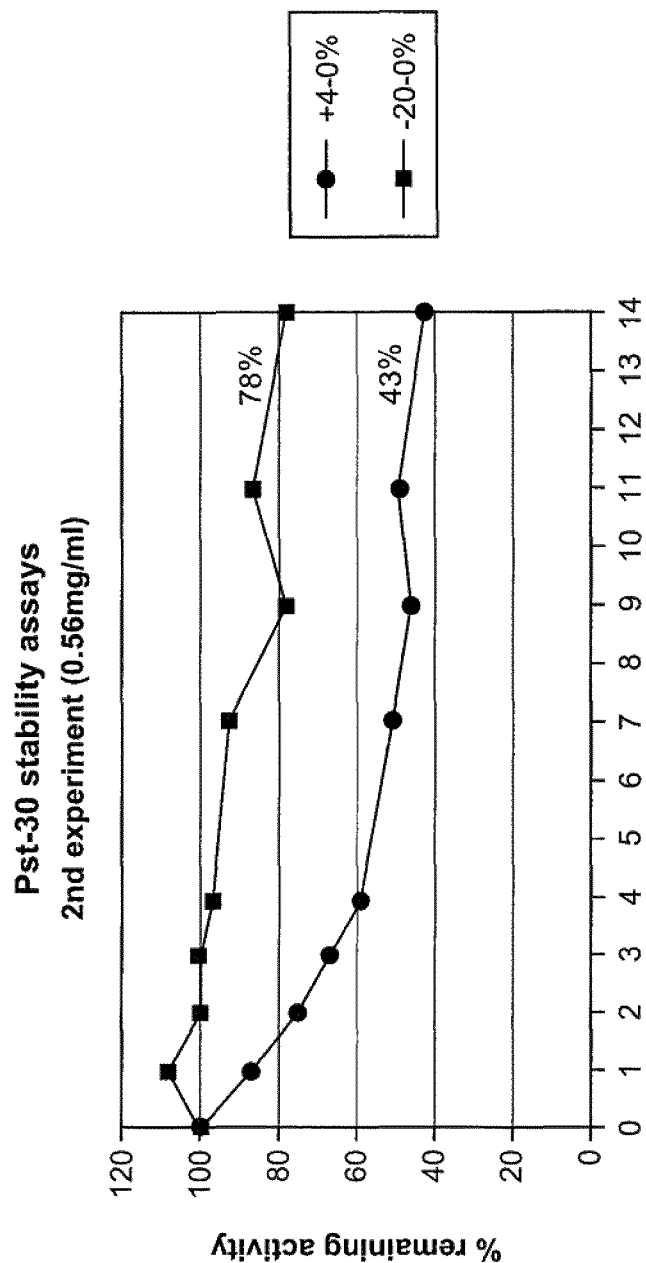
FIG. 10 provides a graph depicting the results PST-30 (MalE-PST-Δ32) stability assays. A concentration of 1.56 mg/ml of PST-30 (MalE-PST-Δ32) was used. Time (in days) is plotted on the X-axis, while remaining activity (%) is plotted on the Y axis.

Proteins were purified by amylose affinity chromatography, and kept at either 4° C. or −20° C. with and without the addition of glycerol. Activity assays were performed as described above and analyzed by CE to determine residual activity as a function of time. As depicted in FIGS. 8, 9 and 10, the PST-30 (MalE-PST-Δ32) preparation is more active than PST-13 (MalE-full length PST) upon storage at 4° C. for up to 2 weeks. Upon the addition of 20% glycerol, the activities of both the PST-13 (MalE-full length PST) and PST-30 (MalE-PST-Δ32) preparations were maintained to a similar extent.

Example 6

Poly-Sialylation of Glycoproteins by Truncated PSTs

Figure 11:
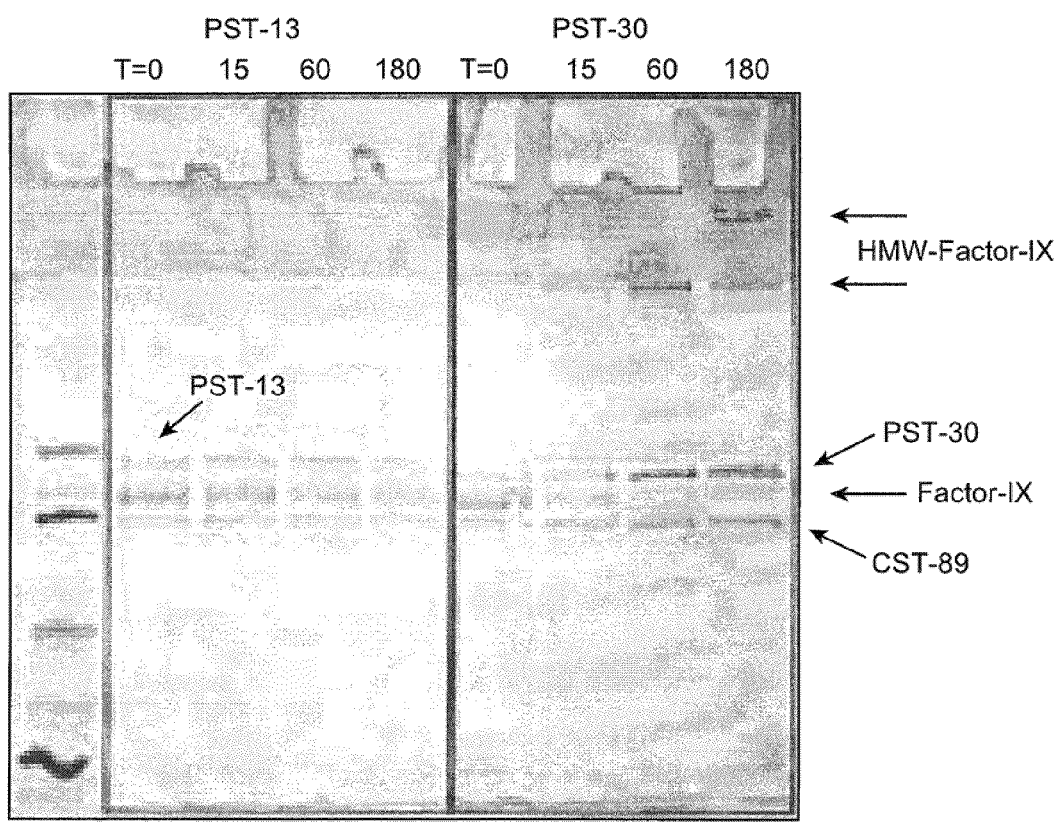
FIG. 11 provides a representative SDS-PAGE analysis of polysialylation of Factor-IX in reactions containing CST-89, a bi-functional sialyltransferase and either PST-13 (MalE-full length PST) or PST-30 (MalE-PST-Δ32). "T" indicates the amount of time (in minutes) the reactions were allowed to proceed.
Figure 12:
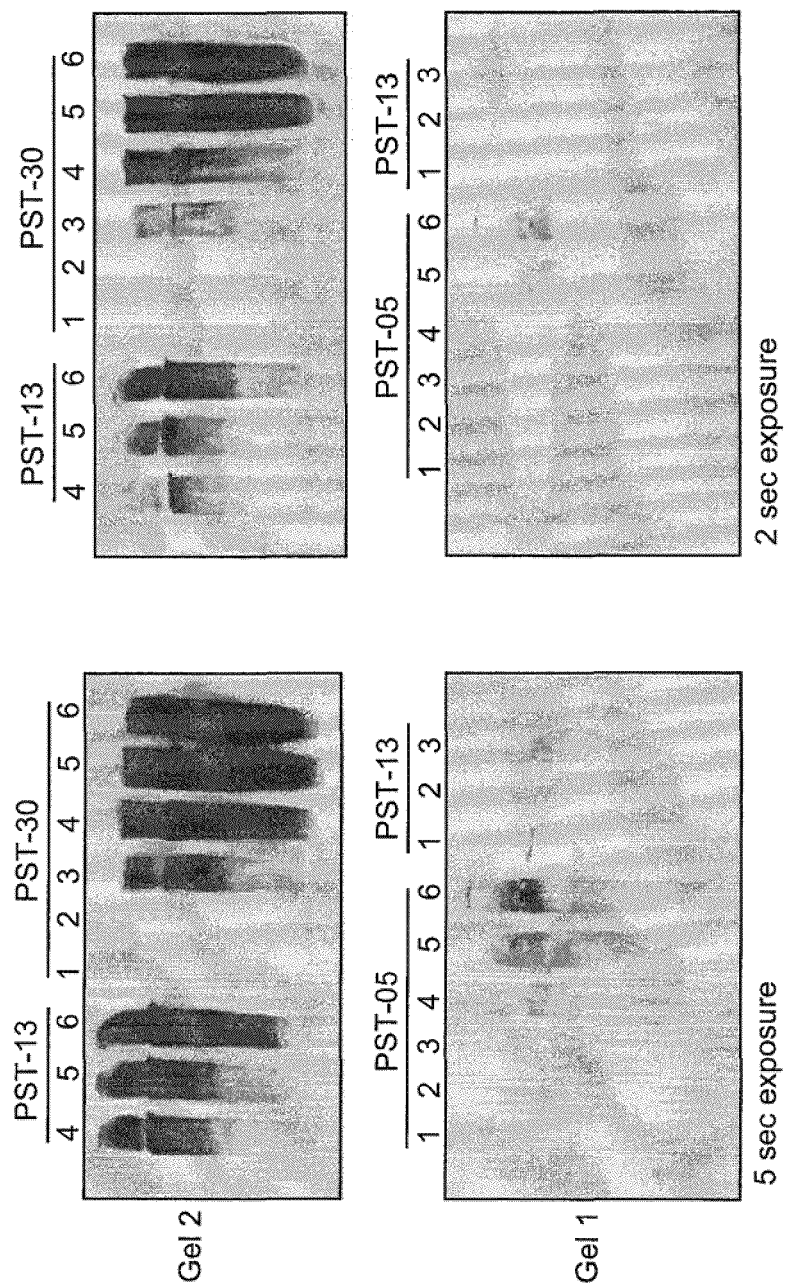
FIG. 12 provides the results of polysialylation of Fetuin by bacterial poly-sialyltransferases. The following enzymes were assayed: *Neisseria* enzymes PST-13 (MalE-full length PST) and PST-30 (MalE-PST-Δ32) and *E. coli* enzyme PST-5. Film was exposed for two or five seconds. The lanes are numbered as follows: Lane 1, no Fetuin control; Lane 2, no CMP-sialic acid control; Lane 3, 1.0 µg PST; Lane 4, 5 µg PST; Lane 5, 10 µg PST; and Lane 6, 15 µg PST.
Figure 13:
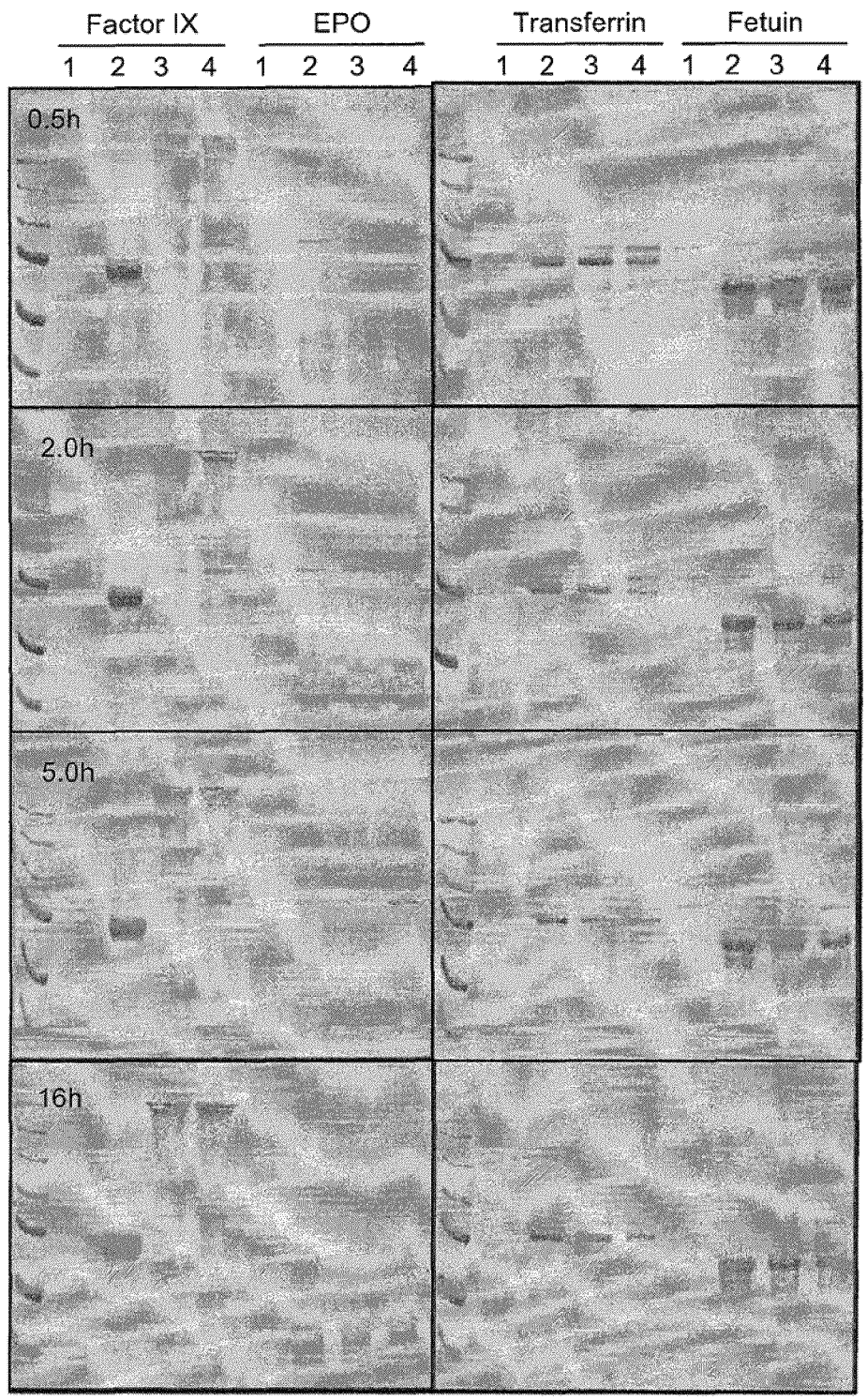
FIG. 13 provides SDS-PAGE analysis of various glycoproteins after incubation with PST-30 (MalE-PST-Δ32) and CMP-sialic acid. The following glycoproteins were assayed: Factor IX, erythropoietin (EPO), Transferrin, and Fetuin. Incubations were 0.5 hours, two hours, 5 hours, and 16 hours. Lane 1, no glycoprotein substrate control; Lane 2, no CMP-sialic acid control; Lane 3, 5.0 µg PST; Lane 4, 15 µg PST.

Factor-IX can be polysialylated with full length PSTs. PSTs from different sources were able to polysialylate Factor-IX to different extents. A comparison of sialylation by PST-13 (MalE-full length PST) and PST-30 (MalE-PST-Δ32) is shown in FIG. 11. Equal amount of PST-13 (MalE-full length PST) and PST-30 (MalE-PST-Δ32) were added to the reactions. PST-30 (MalE-PST-Δ32) in conjunction with CST-89, a bi-specific sialyltransferase utilized for the addition of a first sialic acid residue to the Factor-IX, substrate shifted all of the Factor-IX to high molecular weight material indicating sialylation (FIG. 11). This high molecular weight material corresponds to polysialylated Factor-IX as it showed immunoreactivity with the polysialic acid specific monoclonal antibody 735 obtained from the Hannover Medical School (Hannover, Germany). These results indicate that the more soluble, truncated form of PST from *N. meningitidis* is more active on a therapeutic substrate as evidenced by a nearly complete conversion of Factor-IX to a polysialylated version.

Increasing amounts of PST's were assayed using Fetuin type III as a substrate. Nine milligrams of Fetuin type III was treated with 846 mU of CST-81 (Cst-II from *C. jejuni*) to form a disialylated substrate for the PST enzymes. The disialylated Fetuin type III was then purified using anion exchange (recovery of protein was about 38%).

Assays were performed using increasing amounts of *Neisseria* enzymes: PST-13 (MalE-full length PST) and PST-30 (MalE-PST-Δ32). An *E. coli* PST enzyme, PST-05, was also assayed. Fifty μg of "di-sialyl-fetuin" at 1 mg/mL was incubated with 1, 5, 10, 15 μg purified PST protein in 50 mM TrisHCl pH 8, 10 mM MgCl2, 7.8 mM CMP-NeuAc at 30° C. Samples were taken at 5 min, 1 hour, 2 hours, 4 hours, and overnight and placed at −80° C. to stop the reaction. Both no fetuin and no CMP-NeuAc controls were done for each enzyme. Samples were first analyzed by 8% SDS-PAGE, where 2.5 μL of each reaction was diluted in sample buffer and denatured at 37° C. for ~10 min.

The SDS-PAGE samples were then immunoblotted using monoclonal antibody mAb735, which detects polysialic acid of lengths greater than 8 NeuAc. The primary antibody mAb735 was diluted 1:7500 in blocking buffer and the blots were incubated in this at 4° C. overnight. Bound antibody was detected with goat anti-mouse HRP (Sigma). The blots were then analyzed by exposing to Kodak Biomax light film (Sigma) for 2 to 10 seconds after incubation with luminol reagents (Perkin Elmer) for 60 sec. Immunoblotting results are shown in FIG. 12. The *Neisseria* enzyme, PST-30 (MalE-PST-Δ32), exhibited the highest levels of activity, surpassing the full length *Neisseria* enzyme, PST-13. Also, the *E. coli* PST protein did produce poly-sialic acid (PSA), but at a lower level than the *Neisseria* enzymes.

Side-by-side assays were performed to measure PST-30 (MalE-PST-Δ32) poly-sialylation activity toward Factor IX, human erythropoietin produced in Chinese hamster ovary (CHO) cells (EPO), Transferrin, and Fetuin. The glycoprotein substrates were first incubated with CstII protein from *C. jejuni* to generate the appropriate substrate for the poly-sialyltransferase. Reactions were carried out at 30° C. for two hours and the di-sialylated substrate glycoprotein were purified using a 1 mL HiTrap Q HP column and an increasing gradient of $NH_4HCO_3$, about pH 7.5.

Fifty micrograms of Factor IX, EPO, Transferrin, and Fetuin at 1 mg/mL were incubated with 5 μg and 15 μg of purified PST-30 (MalE-PST-Δ32) in a reaction buffer (50 mM TrisHCl, pH 8.0; 10 mM $MgCl_2$; and 7.8 mM CMP-NeuAc) at 30° C. for the following incubation times: 0.5 hours, 2 hours, 5 hours, and overnight. Samples were removed at each of these time-points and placed at −80° C. to stop the reaction. Controls were also included for each assayed glycoprotein, i.e., no glycoprotein or no CMP-NeuAc. Reaction products (2.5 μL) were diluted in sample buffer and denatured at 37° C. for ~10 min and analyzed by 8% SDS-PAGE. the SDS-PAGE gels are shown in FIG. 13.

Figure 14:
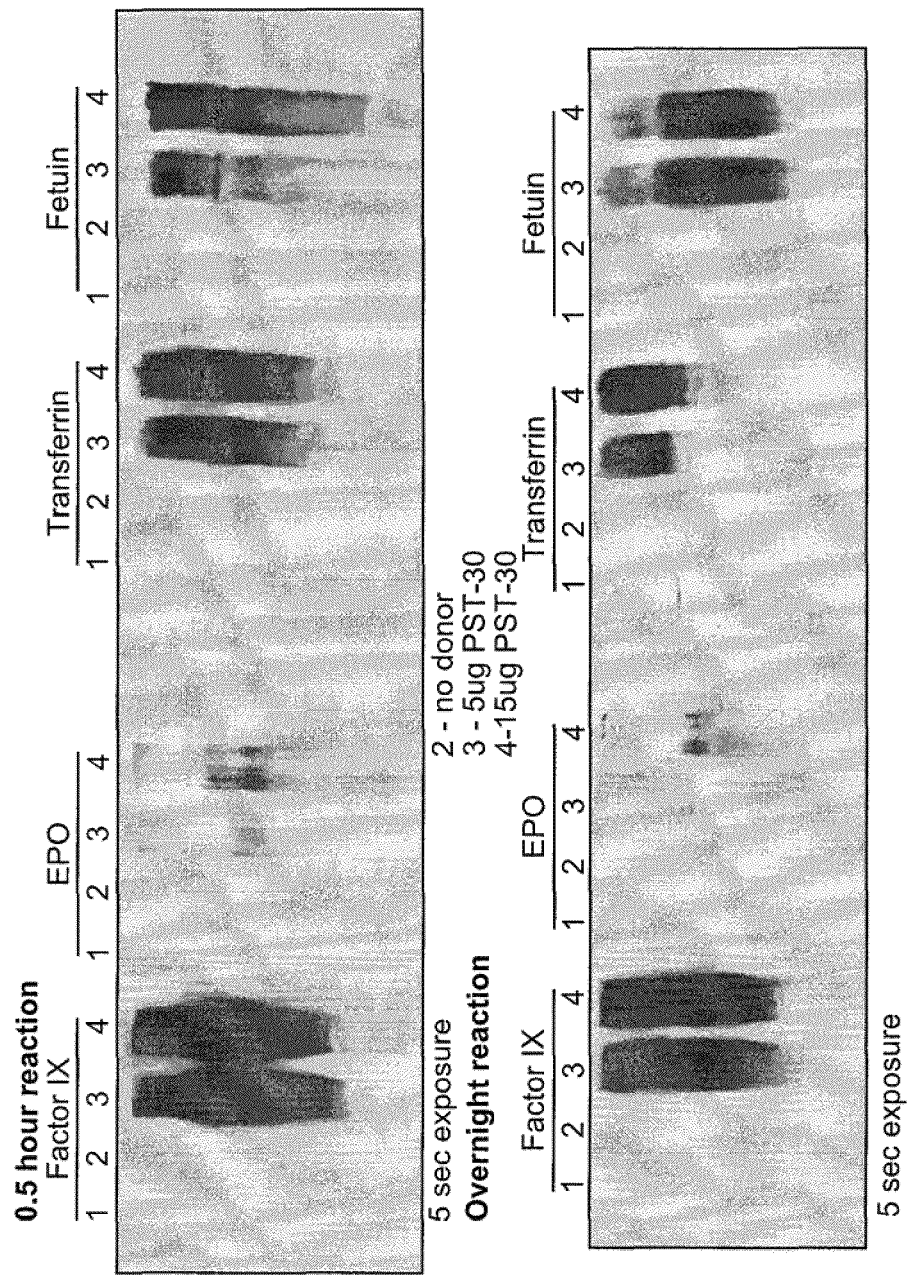
FIG. 14 the results of polysialylation various glycoproteins after incubation with PST-30 (MalE-PST-Δ32) and CMP-sialic acid. The following glycoproteins were assayed: Factor IX, erythropoietin (EPO), Transferrin, and Fetuin. Incubations were 0.5 hours or 16 hours. Lane 1, no glycoprotein substrate control; Lane 2, no CMP-sialic acid control; Lane 3, 5.0 µg PST; Lane 4, 15 µg PST.

The 0.5 hour and overnight time points were then analyzed by western blotting. For the 0.5 hour reactions, 120 ng of protein was loaded on an 8% SDS-PAGE. For the overnight reactions, 30 ng of protein was loaded. Western blotting was performed as described above using mAb735 to detect polysialic acid. Results are shown in FIG. 14. The truncated *Neisseria* PST protein, PST-30 (MalE-PST-Δ32), was able to sialylate each of the mammalian substrate proteins: Factor IX, EPO, Transferrin, and Fetuin.

Example 7

Effect of Glycoprotein Substrate Concentration on Poly-Sialic Acid Chain Length

Varying concentrations of Fetuin were incubated with 7 μg of PST-30 (MalE-PST-Δ32) and 10 mM CMP-NeuAc in 50 mM HEPES pH 7.5, 10 mM MgCl$_2$ at 30° C. for 0.5, 1, 2, 4 hours and overnight. concentrations have more salt in them as the Fetuin was in 20 mM TrisHCl pH 8.0, 50 mM NaCl. 2.5 ug of fetuin from each overnight reaction was analyzed by 8% SDS-PAGE as described above. These samples were then analyzed by immunoblot. Results are shown in FIG. 15. 20 ng of fetuin from each of the 0.5 h, 1 h, and overnight reactions was analyzed by 8% SDS-PAGE and immunoblotted as described above. Overnight reactions done using 5 mg/mL Fetuin substrate not only have shorter PSA chains, but those chains are all more uniform in length (seen as a tighter band as opposed to the long smear in the 0.5 mg/mL reaction).

Example 8

Fusion of Truncated PST to a Sialyltransferase

Fusions of truncated *Neisseria* PSTs to CST-II were active and can be used to produce polysialylated product.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

```
                    INFORMAL SEQUENCE LISTING

SEQ ID NO: 1 siaD from Neisseria meningitidis
   1  mlkkikkalf qpkkffqdsm wlttspfylt pprnnlfvis nlgqlnqvqs likiqkltnn 61  llvilytskn lkmpklvhqs anknlfesiy lfelprspnn itpkkllyiy rsykkilnii 121  qpahlymlsf tghysylisi akkknitthl idegtgtyap llesfsyhpt klerylignn 181  lnikgyidhf dilhvpfpey akkifnakky nrffahaggi sinnnianlq kkyqiskndy 241  ifvsqrypis ddlyyksive ilnsislqik gkifiklhpk emgnnyvmsl flnmveinpr 301  lvvineppfl iepliyltnp kgiiglasss liytpllsps tqclsigeli inliqkysmv 361  entemiqehl eiikkfnfin ilndlngvis nplfkteetf etllksaefa yksknyfqai 421  fywqlasknn itllghkalw yynalynvkq iykmeysdif yidnisvdfh skdkltweki 481  khyyysadnr igrdr SEQ ID NO: 2 MalE-PstNm(-19aa, PST-29)
MKIEEGKLVI WINGDKGYNG LAEVGKKFEK DTGIKVTVEH PDKLEEKFPQ

VAATGDGPDI IFWAHDRFGG YAQSGLLAEI TPDKAFQDKL YPFTWDAVRY

NGKLIAYPIA VEALSLIYNK DLLPNPPKTW EEIPALDKEL KAKGKSALMF

NLQEPYFTWP LIAADGGYAF KYENGKYDIK DVGVDNAGAK AGLTFLVDLI

KNKHMNADTD YSIAEAAFNK GETAMTINGP WAWSNIDTSK VNYGVTVLPT

FKGQPSKPFV GVLSAGINAA SPNKELAKEF LENYLLTDEG LEAVNKDKPL

GAVALKSYEE ELAKDPRIAA TMENAQKGEI MPNIPQMSAF WYAVRTAVIN

AASGRQTVDE ALKDAQTRIT KGGGHIFNPR GSHMWLTTSP FYLTPPRNNL F

VISNLGQLNQ VQSLIKIQKL TNNLLVILYT SKNLKMPKLV HQSANKNLFE

SIYLFELPRS PNNITPKKLL YIYRSYKKIL NIIQPAHLYM LSFTGHYSYL

ISIAKKKNIT THLIDEGTGT YAPLLESFSY HPTKLERNLI GNNLNIKGYI

DHFDILHVPF PEYAKKIFNA KKYNRFFAHA GGISINNNIA NLQKKYQISK

NDYIFVSQRY PISDDLYYKS IVEILNSISL QIKGKIFIKL HPKEMGNNYV

MSLFLNMVEI NPRLVVINEP PFLIEPLIYL TNPKGIIGLA SSSLIYTPLL SPSTQCLSIG
```

-continued

| INFORMAL SEQUENCE LISTING |
| --- |
| ELIINLIQKY SMVENTEMIQ EHLEIIKKFN FINILNDLNG VISNPLFKTE |
| ETFETLLKSA EFAYKSKNYF QAIFYWQLAS KNNITLLGHK ALWYYNALYN |
| VKQIYKMEYS DIFYIDNISV DFHSKDKLTW EKIKHYYYFA DNRIGRDR |
| SEQ ID NO: 3 PstNm(-19aa, PST-29)<br>MWLTTSP FYLTPPRNNL F VISNLGQLNQ VQSLIKIQKL TNNLLVILYT |
| SKNLKMPKLV HQSANKNLFE SIYLFELPRS PNNITPKKLL YIYRSYKKIL |
| NIIQPAHLYM LSFTGHYSYL ISIAKKKNIT THLIDEGTGT YAPLLESFSY |
| HPTKLERNLI GNNLNIKGYI DHFDILHVPF PEYAKKIFNA KKYNRFFAHA |
| GGISINNNIA NLQKKYQISK NDYIFVSQRY PISDDLYYKS IVEILNSISL QIKGKIFIKL |
| HPKEMGNNYV MSLFLNMVEI NPRLVVINEP PFLIEPLIYL TNPKGIIGLA |
| SSSLIYTPLL SPSTQCLSIG ELIINLIQKY SMVENTEMIQ EHLEIIKKFN FINILNDLNG |
| VISNPLFKTE ETFETLLKSA EFAYKSKNYF QAIFYWQLAS KNNITLLGHK |
| ALWYYNALYN VKQIYKMEYS DIFYIDNISV DFHSKDKLTW EKIKHYYYFA |
| DNRIGRDR |
| SEQ ID NO: 4 MalE-PSTNm(-32aa, PST-30)<br>MKIEEGKLVI WINGDKGYNG LAEVGKKFEK DTGIKVTVEH PDKLEEKFPQ |
| VAATGDGPDI IFWAHDRFGG YAQSGLLAEI TPDKAFQDKL YPFTWDAVRY |
| NGKLIAYPIA VEALSLIYNK DLLPNPPKTW EEIPALDKEL KAKGKSALMF |
| NLQEPYFTWP LIAADGGYAF KYENGKYDIK DVGVDNAGAK AGLTFLVDLI |
| KNKHMNADTD YSIAEAAFNK GETAMTINGP WAWSNIDTSK VNYGVTVLPT |
| FKGQPSKPFV GVLSAGINAA SPNKELAKEF LENYLLTDEG LEAVNKDKPL |
| GAVALKSYEE ELAKDPRIAA TMENAQKGEI MPNIPQMSAF WYAVRTAVIN |
| AASGRQTVDE ALKDAQTRIT KGGGHIFNPR GSHMRNNLF VISNLGQLNQ |
| VQSLIKIQKL TNNLLVILYT SKNLKMPKLV HQSANKNLFE SIYLFELPRS |
| PNNITPKKLL YIYRSYKKIL NIIQPAHLYM LSFTGHYSYL ISIAKKKNIT |
| THLIDEGTGT YAPLLESFSY HPTKLERNLI GNNLNIKGYI DHFDILHVPF |
| PEYAKKIFNA KKYNRFFAHA GGISINNNIA NLQKKYQISK NDYIFVSQRY |
| PISDDLYYKS IVEILNSISL QIKGKIFIKL HPKEMGNNYV MSLFLNMVEI |
| NPRLVVINEP PFLIEPLIYL TNPKGIIGLA SSSLIYTPLL SPSTQCLSIG ELIINLIQKY |
| SMVENTEMIQ EHLEIIKKFN FINILNDLNG VISNPLFKTE ETFETLLKSA |
| EFAYKSKNYF QAIFYWQLAS KNNITLLGHK ALWYYNALYN VKQIYKMEYS |
| DIFYIDNISV DFHSKDKLTW EKIKHYYYFA DNRIGRDR |
| SEQ ID NO: 5 PSTNm(-32aa, PST-30)<br>RNNLF VISNLGQLNQ VQSLIKIQKL TNNLLVILYT SKNLKMPKLV HQSANKNLFE |
| SIYLFELPRS PNNITPKKLL YIYRSYKKIL NIIQPAHLYM LSFTGHYSYL |
| ISIAKKKNIT THLIDEGTGT YAPLLESFSY HPTKLERNLI GNNLNIKGYI |
| DHFDILHVPF PEYAKKIFNA KKYNRFFAHA GGISINNNIA NLQKKYQISK |
| NDYIFVSQRY PISDDLYYKS IVEILNSISL QIKGKIFIKL HPKEMGNNYV |
| MSLFLNMVEI NPRLVVINEP PFLIEPLIYL TNPKGIIGLA SSSLIYTPLL SPSTQCLSIG |
| ELIINLIQKY SMVENTEMIQ EHLEIIKKFN FINILNDLNG VISNPLFKTE |
| ETFETLLKSA EFAYKSKNYF QAIFYWQLAS KNNITLLGHK ALWYYNALYN |

---

INFORMAL SEQUENCE LISTING

---

VKQIYKMEYS DIFYIDNISV DFHSKDKLTW EKIKHYYYFA DNRIGRDR

SEQ ID NO: 6
MLKKIKKALFQPKKFFQDSMWLTTSPFYLTPPRNNLFVISNLGQLNQVQSLIK

SEQ ID NO: 7: Sequence of "FLAG tag,"
AspTyrLysAspAspAsp AspLys

SEQ ID NO: 8: Sialyltransferase motif A
DVFRCNQFYFED/E

SEQ ID NO: 9: Sialyltransferase motif B
RITSGVYMC

SEQ ID NO: 10: 5' primer for amplifying E. coli PST
5'-AAGGTATAAGACATATGATATTTGATGCTAGTTTAAAGAAG SEQ ID NO: 11: 3' primer for amplifying E. coli PST
3'-CCTAGGTCGACTTACTCCCCCAAGAAAATCCTTTTATCGTGC

---

What is claimed is:

1. An isolated polysialic acid transferase (PST) polypeptide that comprises an amino acid sequence with 95% identity to SEQ ID NO:5 wherein the PST polypeptide does not comprise an amino acid sequence consisting of amino acids 1-495 of SEQ ID NO: 1, and wherein the PST polypeptide transfers a sialic acid moiety from a donor substrate to an acceptor substrate.

2. The PST polypeptide of claim 1, wherein the PST polypeptide is more soluble than a full length PST polypeptide consisting of amino acids 1-495 of SEQ ID NO: 1.

3. The PST polypeptide of claim 1, further comprising an MBP tag.

4. The PST polypeptide of claim 1, wherein the acceptor substrate is a glycopeptide, a glycoprotein, a glycolipid, or a ganglioside.

5. The PST polypeptide of claim 1, wherein the acceptor substrate is a glycoprotein selected from the group consisting of Factor IX, erythropoietin (EPO), Transferrin, and Fetuin.

6. An isolated truncated polysialic acid transferase (PST) polypeptide that comprises the amino acid sequence of SEQ ID NO: 5.

7. The PST polypeptide of claim 6, further comprising an MBP tag.

8. A method of producing a poly-sialylated product saccharide, the method comprising the step of:
 a) contacting an acceptor substrate with a donor substrate comprising a sialic acid moiety and the PST polypeptide of claim 1; and
 b) allowing transfer of the sialic acid moiety to the acceptor saccharide to occur, thereby producing the poly-sialylated product saccharide.

9. A method of producing a poly-sialylated protein or peptide, the method comprising the step of:
 a) contacting an acceptor substrate with a donor substrate comprising a sialic acid moiety and the PST polypeptide of claim 1; and
 b) allowing transfer of the sialic acid moiety to the acceptor saccharide to occur, thereby producing the poly-sialylated protein or peptide.

10. A method of producing a poly-sialylated glycolipid or ganglioside, the method comprising the step of:
 a) contacting an acceptor substrate with a donor substrate comprising a sialic acid moiety and the PST polypeptide of claim 1; and
 b) allowing transfer of the sialic acid moiety to the acceptor saccharide to occur, thereby producing the poly-sialylated glycolipid or ganglioside.

* * * * *